(12) United States Patent
Yoshikawa et al.

(10) Patent No.: US 12,064,317 B2
(45) Date of Patent: Aug. 20, 2024

(54) DENTAL OBSERVATION DEVICE AND METHOD FOR DISPLAYING DENTAL IMAGE

(71) Applicant: J. MORITA MFG. CORP., Kyoto (JP)

(72) Inventors: Hideki Yoshikawa, Kyoto (JP); Tomoyuki Sadakane, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 1069 days.

(21) Appl. No.: 16/651,647

(22) PCT Filed: Sep. 26, 2018

(86) PCT No.: PCT/JP2018/035604
§ 371 (c)(1),
(2) Date: Mar. 27, 2020

(87) PCT Pub. No.: WO2019/065700
PCT Pub. Date: Apr. 4, 2019

(65) Prior Publication Data
US 2020/0305702 A1    Oct. 1, 2020

(30) Foreign Application Priority Data

Sep. 29, 2017    (JP) ................................ 2017-191359

(51) Int. Cl.
*A61C 9/00*    (2006.01)
*A61B 1/00*    (2006.01)
(Continued)

(52) U.S. Cl.
CPC ...... *A61C 9/0053* (2013.01); *A61B 1/000094* (2022.02); *A61B 1/000095* (2022.02);
(Continued)

(58) Field of Classification Search
CPC ....... A61C 9/0053; A61C 19/041; A61C 5/40; A61B 1/000094; A61B 1/000095;
(Continued)

(56) References Cited

U.S. PATENT DOCUMENTS

2001/0046316 A1* 11/2001 Miyano ................ A61B 5/0064
348/E13.072
2014/0342301 A1   11/2014 Fleer et al.
(Continued)

FOREIGN PATENT DOCUMENTS

EP    2774543 A1    9/2014
EP    3153129 A1    4/2017
(Continued)

OTHER PUBLICATIONS

Office Action dated Dec. 14, 2021, issued by Japan Patent Office in counterpart JP application No. 2019-545546, in Japanese (4 pages).
(Continued)

*Primary Examiner* — Peter Luong
(74) *Attorney, Agent, or Firm* — Capitol City TechLaw, PLLC; Samuel P. Burkholder

(57) ABSTRACT

A dental observation device by which, without displaying, in an overlapping manner, a visible light image of an image-capturing site in an oral cavity captured by a 3-D camera and 3-D image information on the image-capturing site in the oral cavity acquired in advance, an invisible portion in the visible light image is easily recognized.

An observation system includes a visible light 3-D camera; a relative position calculator; a 3-D information storage storing 3-D image information acquired in advance; an image display displaying, side by side, a 2-D captured image captured by the visible light 3-D camera and 2-D converted image based on the 3-D image information corresponding to the surgical operation target site; and a display direction
(Continued)

adjuster displaying, in the image display, the 2-D converted image in a predetermined direction on the basis of the image-capturing direction detected by the relative position calculator.

18 Claims, 14 Drawing Sheets

(51) Int. Cl.
| | |
|---|---|
| *A61B 1/04* | (2006.01) |
| *A61B 1/24* | (2006.01) |
| *A61B 5/00* | (2006.01) |
| *A61B 5/055* | (2006.01) |
| *A61B 6/03* | (2006.01) |
| *A61B 6/51* | (2024.01) |
| *A61B 8/08* | (2006.01) |
| *A61B 90/00* | (2016.01) |
| *A61B 90/25* | (2016.01) |
| *A61C 19/04* | (2006.01) |
| *H04N 13/239* | (2018.01) |
| *H04N 13/254* | (2018.01) |
| *A61B 34/00* | (2016.01) |
| *H04N 13/00* | (2018.01) |

(52) U.S. Cl.
CPC .......... *A61B 1/0002* (2013.01); *A61B 1/0005* (2013.01); *A61B 1/00193* (2013.01); *A61B 1/00194* (2022.02); *A61B 1/04* (2013.01); *A61B 1/24* (2013.01); *A61B 5/0035* (2013.01); *A61B 5/0088* (2013.01); *A61B 5/055* (2013.01); *A61B 6/032* (2013.01); *A61B 6/51* (2024.01); *A61B 8/483* (2013.01); *A61B 90/25* (2016.02); *A61B 90/361* (2016.02); *A61C 19/041* (2013.01); *H04N 13/239* (2018.05); *H04N 13/254* (2018.05); *A61B 34/25* (2016.02); *A61B 2090/368* (2016.02); *A61B 2090/373* (2016.02); *A61B 2090/374* (2016.02); *A61B 2090/3762* (2016.02); *A61B 2090/378* (2016.02); *H04N 2013/0085* (2013.01)

(58) Field of Classification Search
CPC . A61B 1/0002; A61B 1/0005; A61B 1/00193; A61B 1/00194; A61B 1/04; A61B 1/24; A61B 5/0035; A61B 5/0088; A61B 5/055; A61B 6/032; A61B 6/14; A61B 8/483; A61B 90/25; A61B 90/361; A61B 34/25; A61B 2090/368; A61B 2090/373; A61B 2090/374; A61B 2090/3762; A61B 2090/378; H04N 13/239; H04N 13/254; H04N 13/271; H04N 2013/0085; H04N 2213/001; G16H 30/20; G16H 30/40; G16H 20/40; G02B 21/0012; G02B 21/365

See application file for complete search history.

(56) References Cited

U.S. PATENT DOCUMENTS

| | | | |
|---|---|---|---|
| 2015/0064643 | A1 | 3/2015 | Chun et al. |
| 2015/0297311 | A1* | 10/2015 | Tesar ................ G02B 21/0012 600/109 |
| 2017/0065370 | A1 | 3/2017 | Nakai |
| 2017/0071713 | A1 | 3/2017 | Nakai |
| 2017/0209035 | A1 | 7/2017 | Li |
| 2019/0327394 | A1* | 10/2019 | Ramirez Luna ....... H04N 23/51 |

FOREIGN PATENT DOCUMENTS

| | | | |
|---|---|---|---|
| EP | 3743010 | A1 | 12/2020 |
| JP | 2011024820 | A | 2/2011 |
| JP | 2011030637 | A | 2/2011 |
| JP | 2012016573 | A | 1/2012 |
| JP | 2014171488 | A | 9/2014 |
| JP | 2015223324 | A | 12/2015 |
| WO | 2015178452 | A1 | 11/2015 |
| WO | 2015182651 | A1 | 12/2015 |
| WO | 2019147984 | A1 | 8/2019 |

OTHER PUBLICATIONS

Machine translation to English of Office Action dated Dec. 14, 2021, issued by Japan Patent Office in counterpart JP application No. 2019-545546 (10 pages).
Office Action dated Mar. 31, 2021, issued by Japan Patent Office in counterpart JP application No. 2019-545546, in Japanese (4 pages).
Machine translation to English of Office Action dated Mar. 31, 2021, issued by Japan Patent Office in counterpart JP application No. 2019-545546 (9 pages).
Extended European Search Report dated May 25, 2021, issued by European Patent Office in counterpart EP application No. 18 86 1405.1 (12 pages).
Office Action dated May 27, 2022, issued by European Patent Office in counterpart EP application No. 18 861 405.1 (8 pages).

* cited by examiner

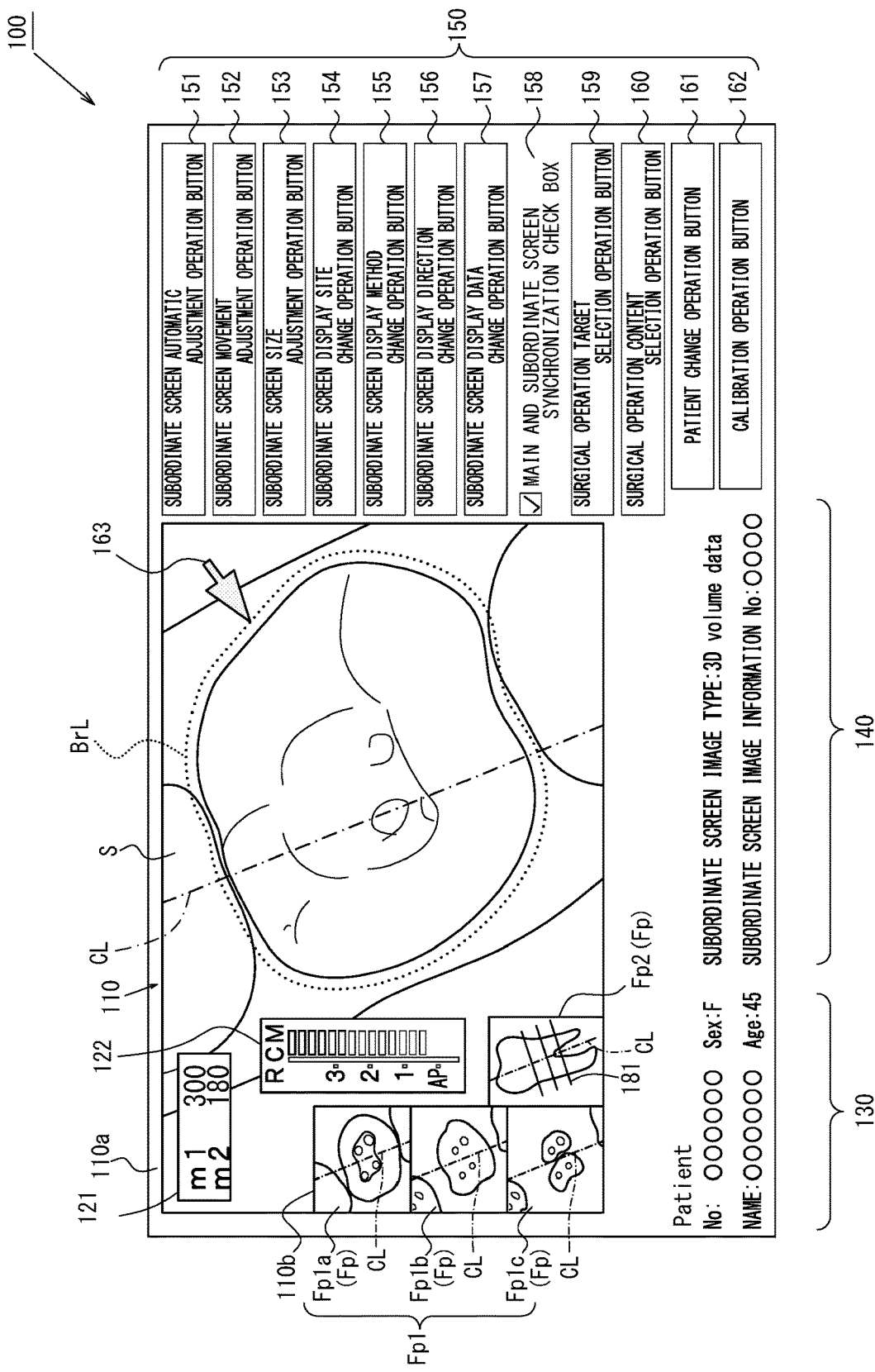

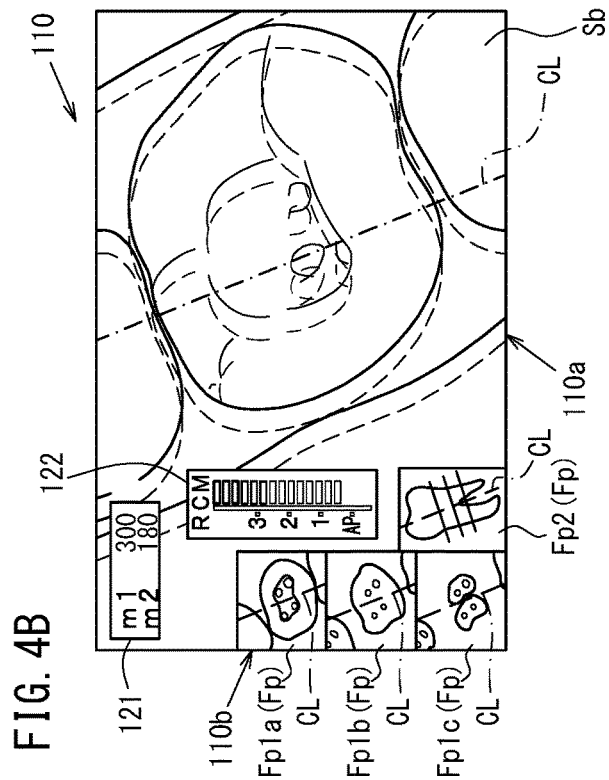
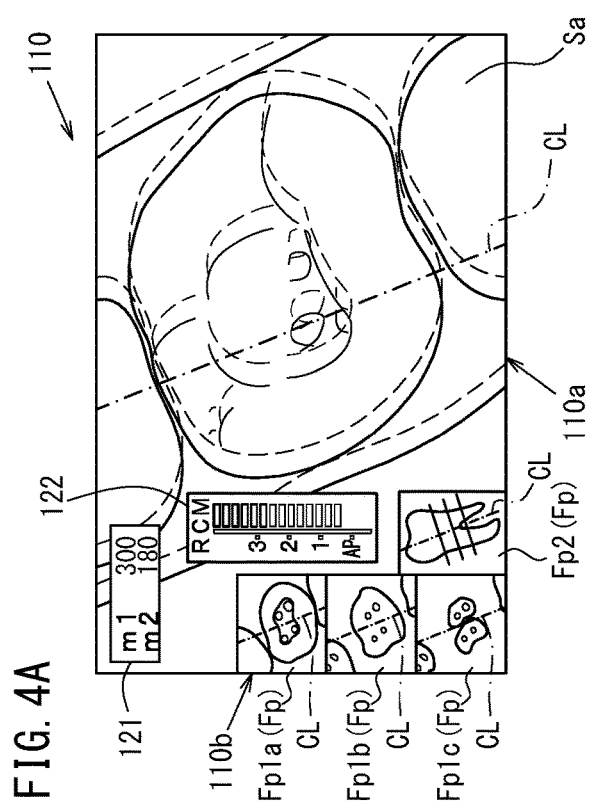
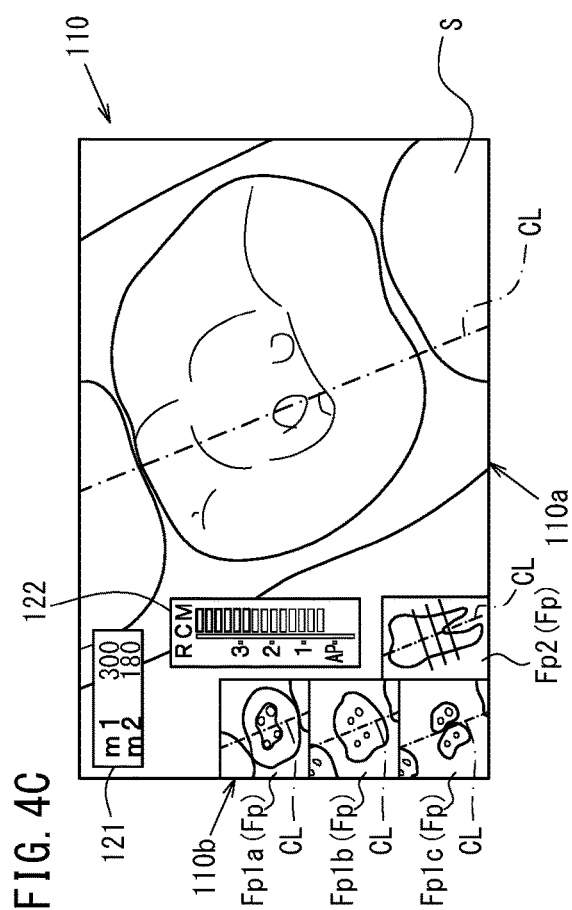

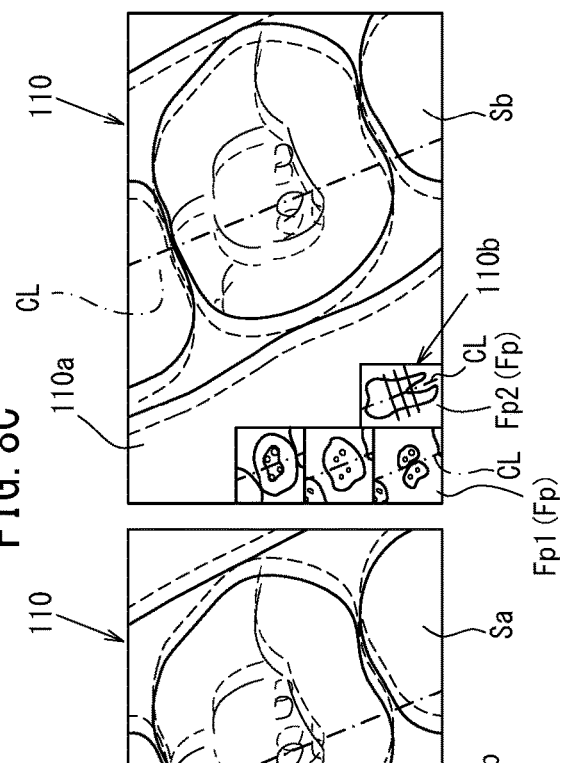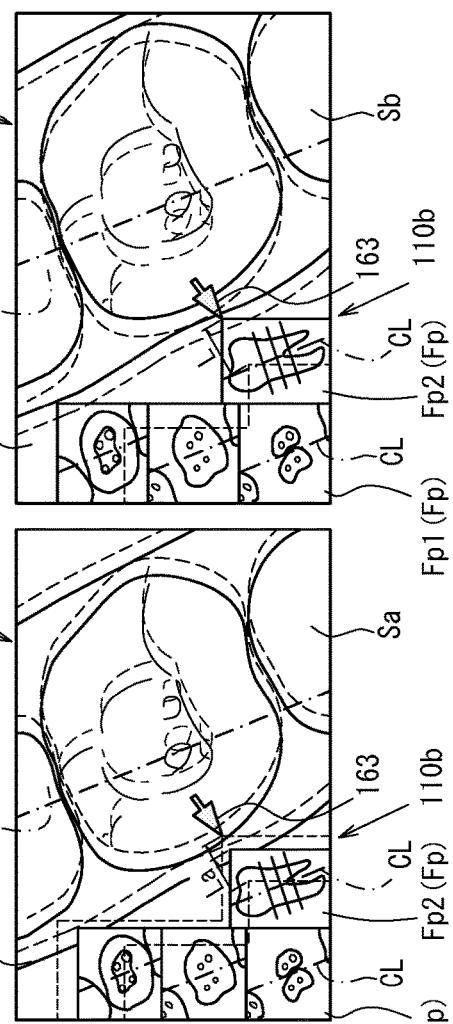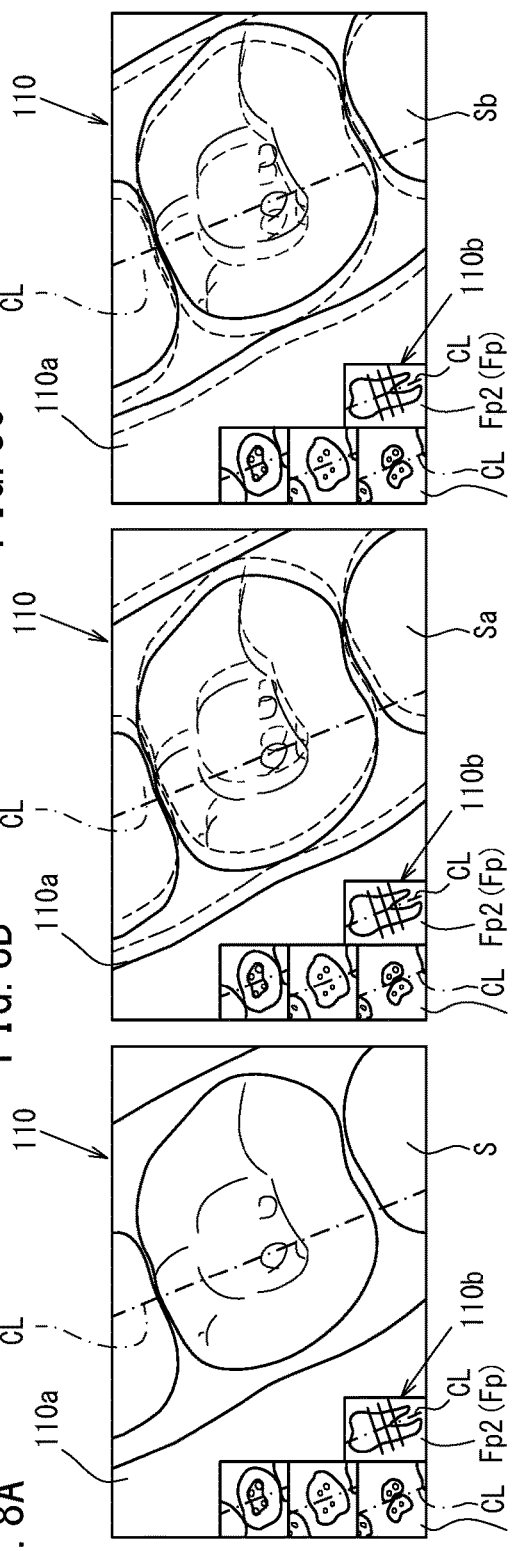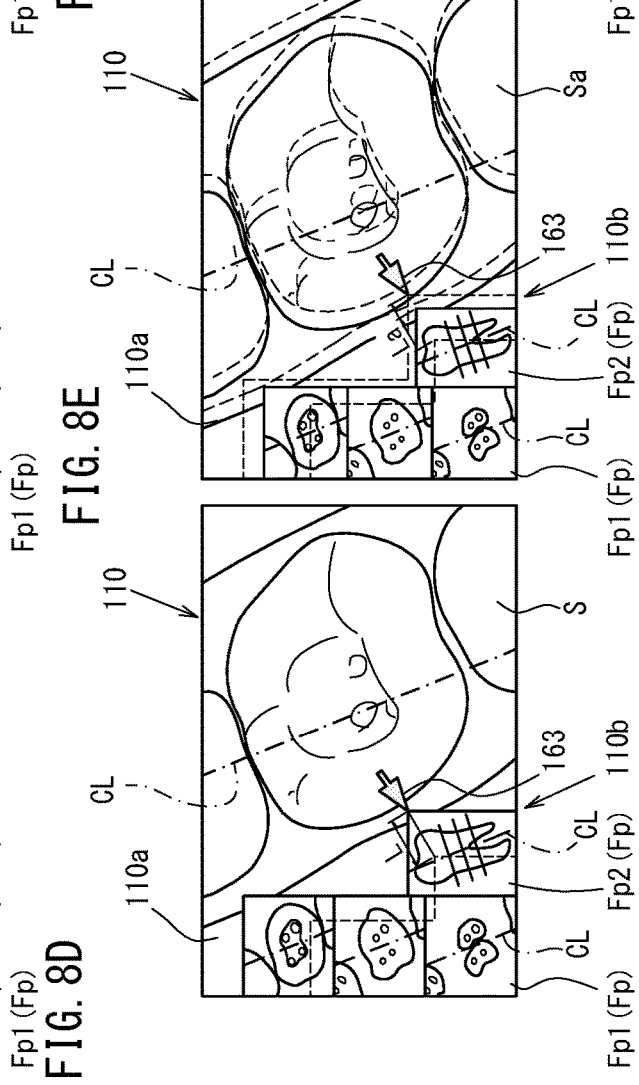

FIG. 11A
FIG. 11B
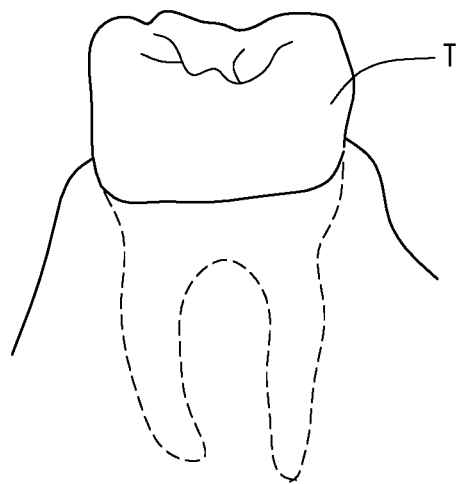
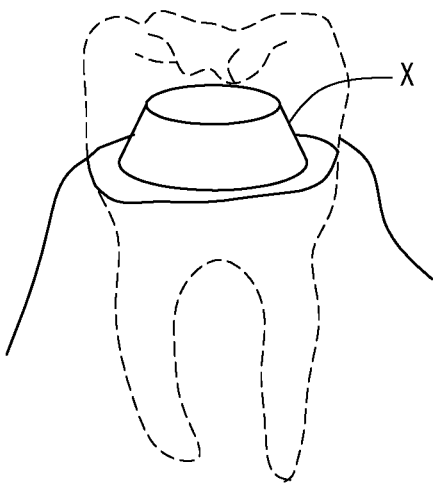

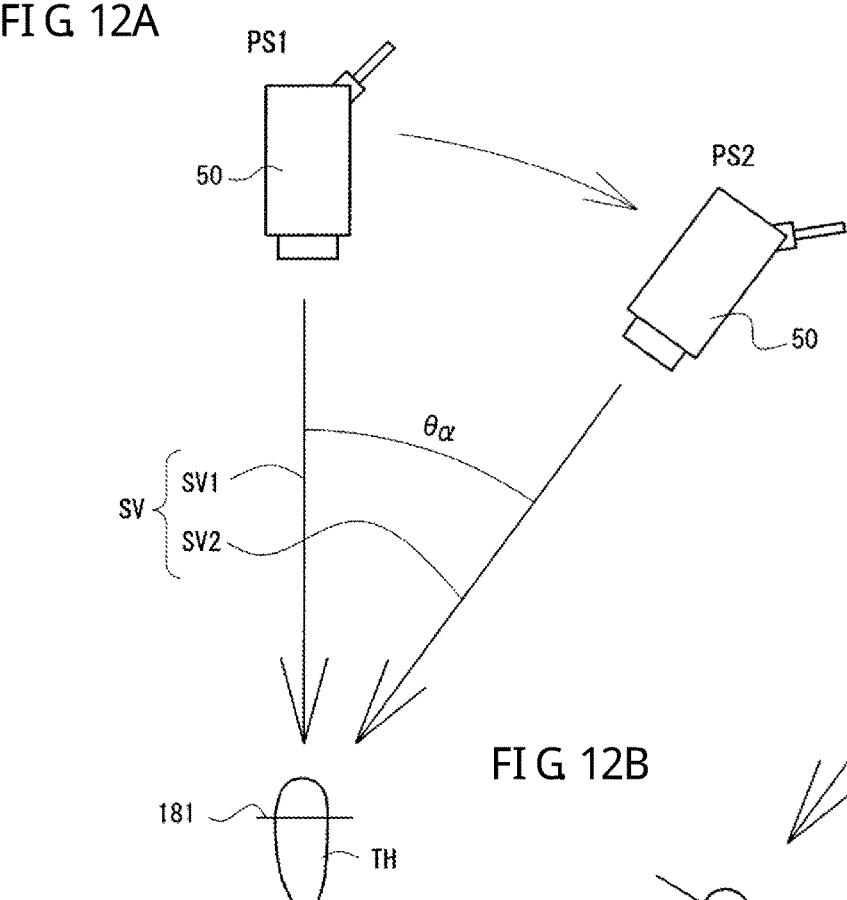
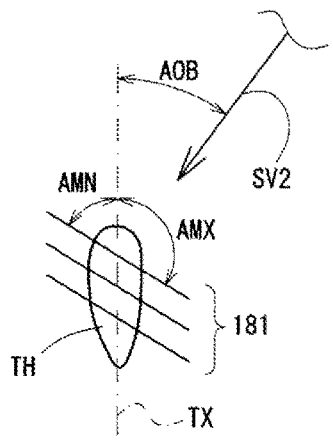
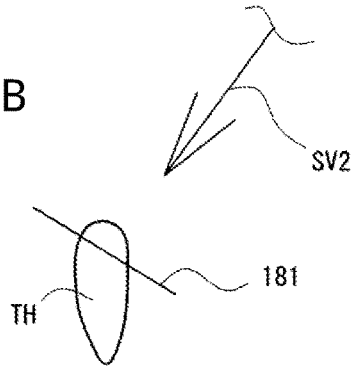
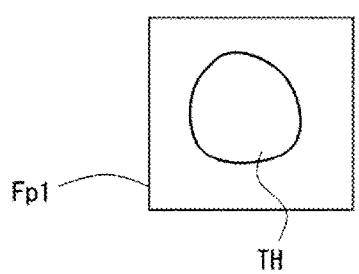
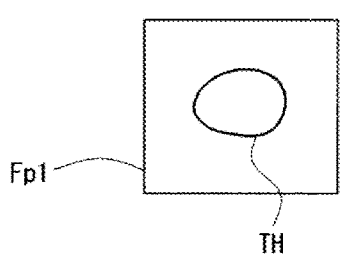

FIG. 13A
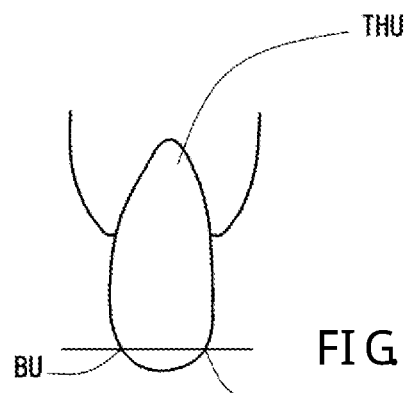
FIG. 13B
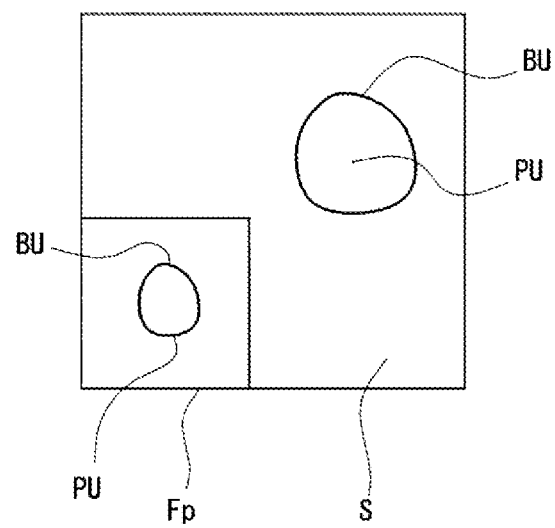
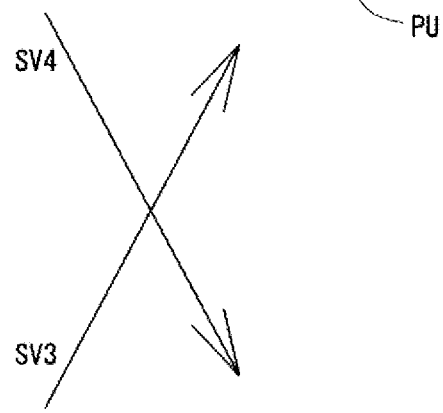
FIG. 13C
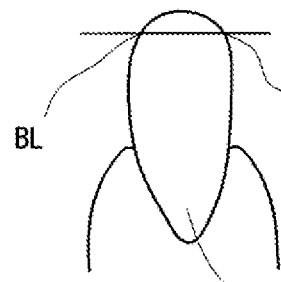
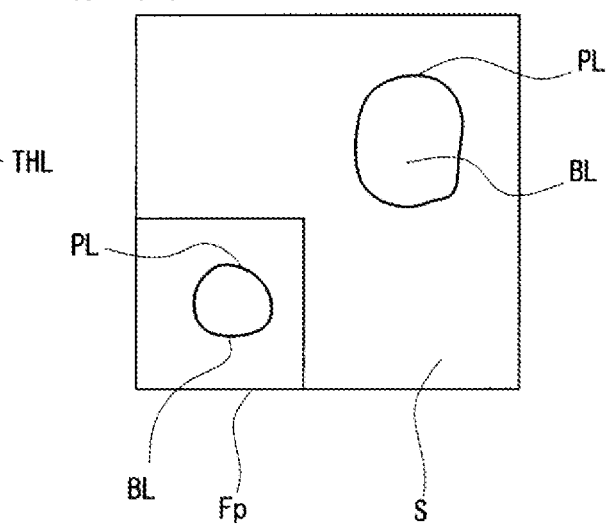

DENTAL OBSERVATION DEVICE AND METHOD FOR DISPLAYING DENTAL IMAGE

CROSS-REFERENCE TO RELATED APPLICATION

This application is a U.S. National Stage Application under 35 U.S.C. § 371 of International Application No. PCT/JP2018/035604 filed Sep. 26, 2018, which claims the benefit of priority to Japanese Patent Application No. 2017-191359 filed Sep. 29, 2017, the disclosures of all of which are hereby incorporated by reference in their entities.

TECHNICAL FIELD

The present invention relates to a dental observation device displaying a visible light image of a desired image-capturing site in, for example, an oral cavity region and a corresponding image based on three-dimensional image information corresponding to the image-capturing site, and a method for displaying a dental image.

BACKGROUND ART

Conventionally in the dental-medical field and the like, in order to perform a treatment on, for example, the root canal of a tooth, an image of the oral cavity or tooth is captured (observed) by an optical camera called an "oral camera" or a dental microscope, in general. Thus, the treatment on the root canal or like of the tooth is performed precisely.

However, a visible light image captured by such an optical camera or a dental microscope is an image of a surface of the tooth in an articulation face direction. It is difficult to check the form of an invisible portion such as, for example, the root canal inside the tooth with such a visible light image.

In order to solve such a problem, Japanese Laid-Open Patent Publication No. 2015-223324 (Patent Document 1) discloses a root canal treatment device. This root canal treatment device directs an x-ray toward a tooth in a region of interest to collect projection data and reconstructs the acquired projection data on a computer to generate a computerized tomographic image (CT image, volume rendering image, etc.), namely, performs CT image capturing. The root canal treatment device also uses the x-ray transmitted through the tooth to display the form or the like, namely, the position or the size of the root canal, which is invisible from the surface of the tooth, on the visible light image of the tooth, which is the region of interest, in an overlapping manner.

The root canal treatment device allows an operation worker to perform a treatment in the state where the invisible portion is visualized. The operation worker does not need to three-dimensionally synthesize, in mind, the CT image and the visible light image captured by the optical camera or the dental microscope. Therefore, the treatment is performed more safely and more accurately.

As can be seen, it is preferable that the operation worker performs a treatment while checking a visible light image on which the invisible portion in a visualized state is displayed in an overlapping manner, with no need to three-dimensionally synthesize, in mind, the CT image of the invisible portion and the visible light image captured by the optical camera or the dental microscope. Nonetheless, it is also desired to prioritize the visibility of the site on which the surgical operation is to be performed.

CITATION LIST

Patent Literature

Patent Document 1: Japanese Laid-Open Patent Publication No. 2015-223324

SUMMARY OF INVENTION

Technical Problem

In such a situation, the present invention has an object of providing a dental observation device and a method for displaying a dental image with which in the state where a visible light image of a desired image-capturing site in an oral cavity region captured by a three-dimensional camera and three-dimensional image information on the desired image-capturing site in the oral cavity region acquired in advance are not displayed in an overlapping manner, an invisible portion of the visible light image is easily recognized.

Solution to the Problem

The present invention is directed to a dental observation device including a three-dimensional camera performing three-dimensional image capturing of a visible light image of a desired image-capturing site in an oral cavity region; an image-capturing direction detector detecting an image-capturing direction of the three-dimensional camera for the image-capturing site; a storage portion storing three-dimensional image information on the oral cavity region acquired in advance; a display portion displaying, side by side, the visible light image captured by the three-dimensional camera and a corresponding image based on the three-dimensional image information corresponding to the image-capturing site; and an image processor displaying, on the display portion, the corresponding image in a predetermined direction on the basis of the image-capturing direction detected by the image-capturing direction detector.

The present invention is also directed to a method for displaying a dental image, including the steps of performing, by a three-dimensional camera, three-dimensional image-capturing of a visible light image of a desired image-capturing site in an oral cavity region; and displaying, side by side, the visible light image captured by the three-dimensional camera and a corresponding image based on a part of three-dimensional image information on the oral cavity region acquired in advance, the part corresponding to the image-capturing site. The corresponding image is displayed in a predetermined direction on the basis of an image-capturing direction of the three-dimensional camera for the image-capturing site.

The three-dimensional camera is capable of capturing, three-dimensionally, the image of the image-capturing site, which is the observation target. The three-dimensional camera is, for example, a two-lens dental microscope that performs the observation using the parallax between the left and right eyes, a head mountable display with a camera, or a device that includes a single lens but acquires depth information. The device that includes a single lens but acquires depth information is, for example, a device acting as including two eyes, an RGB-D camera including both of a component detecting RGB signals as the three primary colors of light and a component detecting the depth, or a light field camera. These devices may each have a structure of displaying the captured information by a flatbed display device such as a liquid crystal display device, an organic EL display device or the like.

The three-dimensional information may be, for example, an x-ray CT image, a nuclear magnetic resonance image, an ultrasonic three-dimensional image, an optical interference tomographic image, three-dimensional scanning data acquired by a three-dimensional oral cavity scanner, or stl data in a file format for 3D CAD software.

The visible light image may be a moving image (video), one of still images provided in a frame-by-frame manner, or the like.

The predetermined direction on the basis of the image-capturing direction is a direction parallel to the image-capturing direction, a direction perpendicular to the image-capturing direction, or a direction having a predetermined angle with respect to the image-capturing direction. In the case where the predetermined direction is the direction parallel to the image-capturing direction, such a direction has the same angle around the image-capturing direction.

The image-capturing direction detector detecting the image-capturing direction of the three-dimensional camera with respect to the image-capturing site may be, for example, a well-known contactless three-dimensional position detector; more specifically, for example, a well-known three-dimensional position measuring device using a gyrosensor built in the three-dimensional camera, an infrared reflective member formed of a plurality of small spheres attached to the three-dimensional camera, and infrared light usable to measure the three-dimensional position of the infrared reflective member. Alternatively, the image-capturing direction detector may be a three-dimensional position measuring device detecting the three-dimensional position by use of a magnetic force generated by a magnetic force generator attached to the three-dimensional camera. Still alternatively, the image-capturing direction detector may be a three-dimensional position induction detector using an image recognition technology or the like based on the image captured by the three-dimensional camera.

The image-capturing direction detector may detect the image-capturing direction of the three-dimensional camera with respect to the image-capturing site based on the position information on the three-dimensional camera and the image-capturing site detected by the position detector.

In this specification, the three-dimensional camera merely needs to capture an image of the image-capturing site for observation or diagnosis. The three-dimensional camera may or may not be capable of recording an image or video.

According to the present invention, the visible light image of a desired image-capturing site in the oral cavity region captured by the three-dimensional camera, and the three-dimensional image information on the desired image-capturing site in the oral cavity region acquired in advance, do not overlap each other, and in this state, an invisible portion in the visible light image is easily recognized.

This will be described in more detail. The image-capturing direction of the three-dimensional camera, performing three-dimensional capturing of the visible light image of a desired image-capturing site in the oral cavity region, with respect to the image-capturing site is detected. The visible light image captured by the three-dimensional camera, and the corresponding image based on the three-dimensional image information that corresponds to the image-capturing site and is acquired in advance and stored on the storage, are displayed side by side in the display portion. The corresponding image in a predetermined direction on the basis of the image-capturing direction detected by the image-capturing direction detector is also displayed.

Therefore, for example, in the state where the corresponding image based on the three-dimensional image information does not overlap the visible light image of the surgical operation target site, the corresponding image in the image-capturing direction of the visible light image of the surgical operation target site is displayed side by side with the visible light image in a direction parallel to the image-capturing direction and at the same angle around the image-capturing direction as the corresponding image. In addition, the corresponding image is displayed in a direction facing the visible light image. Therefore, the operation worker may perform the surgical operation safely and accurately while checking the corresponding image displaying the invisible portion side by side with the invisible portion of the visible image and also while checking the visible light image clearly displaying the surgical operation target site. It is desirable that the corresponding image is displayed at a magnification ratio equal to, or smaller than, that of the captured image.

In an embodiment according to the present invention, the visible light image of the image-capturing site obtained as a result of three-dimensional observation may be displayed three-dimensionally based on left/right parallax, and the corresponding image may be displayed two-dimensionally, as being viewed in a direction parallel to the image-capturing direction and at the same angle around the image-capturing direction as that of the visible light image.

The three-dimensional camera may be a two-lens camera (binocular type camera) or a single-lens camera capable of capturing a three-dimensional image.

According to the present invention, the image-capturing site is displayed three-dimensionally based on the parallax.

The visible light image of the image-capturing site displayed three-dimensionally and the corresponding image displayed two-dimensionally are displayed side by side with no overlapping.

In an embodiment according to the present invention, the display portion may include a corresponding image display region in which the corresponding image is allowed to be displayed, and may also include a region adjuster adjusting at least one of a size and a position of the corresponding image display region in the display portion.

According to the present invention, for example, the corresponding image display region displaying the corresponding image may be position-adjusted to a position that is more easily recognized, enlarged or diminished in accordance with the surgical operation content or the like. Thus, a demand of the operation worker is precisely fulfilled, and the degree of satisfaction of the operation worker is improved.

In an embodiment according to the present invention, the dental observation device may further include a surgical operation target selector selecting a surgical operation target site in the visible light image of the image-capturing site. Based on the positional relationship between a surgical operation target site, selected by the surgical operation target selector, in each of a left parallax image and a right parallax image corresponding to the visible light image and the corresponding image display region, the region adjuster may adjust the corresponding image display region such that the surgical operation target site in each of the left and right parallax images and the corresponding image display region do not overlap each other.

According to the present invention, the surgical operation target site may be selected, in the visible light image of the image-capturing site displayed three-dimensionally, by use of the surgical operation target selector. The three-dimensional display of the surgical operation target site selected in the visible light image of the image-capturing site, and the corresponding image display region displaying the corresponding image two-dimensionally, do not overlap each other, and the corresponding image is adjusted to be at a desired position or to have a desired size.

This will be described specifically. The left and right parallax images in the visible light image show the surgical operation target site at different positions. By contrast, the position of the corresponding image display region displayed two-dimensionally is the same in the left and right parallax images. Therefore, the relative positions of the surgical operation target site in each of the left and right parallax images and the corresponding image display region may be different from each other.

Therefore, in the case where the corresponding image display region is adjusted by the region adjustor, there may be an undesirable possibility that even if the surgical operation target site in one of the left and right parallax images does not overlap the corresponding image display region, the surgical operation target site in the other of the left and right parallax images overlaps the corresponding image display region. Under such a situation, the adjustment on the corresponding image display region by use of the region adjuster is performed, such that the surgical operation target site in any one of the left and right parallax images does not overlap the corresponding image display region based on the positional relationship between the surgical operation target site in each of the left and right parallax images and the corresponding image display region. Therefore, the surgical operation target site displayed three-dimensionally and the corresponding image display region displayed two-dimensionally are displayed side by side with no overlapping.

In an embodiment according to the present invention, the dental observation device may further include a display direction change operator operating a change in the display direction of the corresponding image; and a display direction reset operator performing an operation of returning the display direction of the corresponding image, which has been changed, to a direction corresponding to the image-capturing direction.

According to the present invention, the operation worker may adjust the display direction of the corresponding image by use of the display direction change operator in accordance with the surgical operation. Even after the display direction of the corresponding image is changed, the display direction reset operator may be operated to display the corresponding image, the display direction of which has been changed, in a display direction in accordance with the image-capturing direction of the visible light image with no need to fine-tune the display direction of the corresponding image.

Even in the case where the display direction of the corresponding image is adjusted by use of the display direction change operator and after that, the image-capturing direction of the visible light image is adjusted, the post-adjustment display direction of the corresponding image may be matched to the post-adjustment image-capturing direction of the visible light image. In this case, the convenience and the operability are improved as compared with the case where the post-adjustment display direction of the corresponding image is manually fine-tuned to the post-adjustment image-capturing direction of the visible light image.

In an embodiment according to the present invention, the three-dimensional image information may represent anyone of a three-dimensional x-ray image acquired by an x-ray CT image-capturing device, a nuclear magnetic resonance image acquired by a nuclear magnetic resonance image-capturing device, an ultrasonic three-dimensional image acquired by an ultrasonic diagnostic image-capturing device, and an optical interference three-dimensional image acquired by an optical interference tomographic image-capturing device.

According to the present invention, for example, the three-dimensional image suitable to the surgical operation content or the patient is usable as the three-dimensional image information.

In an embodiment according to the present invention, based on the three-dimensional image information, the image processor may cause the display portion to display a cross-sectional image in a direction based on the image-capturing direction, the cross-sectional image being displayed as the corresponding image.

According to the present invention, the invisible portion in the image-capturing site is recognized more easily and more accurately by the cross-sectional view. Thus, the surgical operation is performed more safely and more accurately.

The cross-sectional view in the direction based on the image-capturing direction may be a cross-sectional view in a direction perpendicular to the image-capturing direction, a vertical cross-sectional view in a direction along the image-capturing direction, or a horizontal cross-sectional view in a direction crossing the image-capturing direction.

In an embodiment according to the present invention, the image processor may include a cross-section adjustment operator adjusting a cross-sectional position in a direction based on the image-capturing direction of the cross-sectional image.

According to the present invention, the cross-sectional view of the invisible portion at a desired cross-sectional position in the image-capturing target is displayed in the display portion. Therefore, the portion of interest in the invisible portion is recognized more easily and more accurately. Thus, the surgical operation is performed more safely and more accurately.

In an embodiment according to the present invention, the three-dimensional image information may represent anyone of three-dimensional scanning data on a surface shape of a tooth region acquired by a three-dimensional oral cavity scanner, three-dimensional information on an implant, and three-dimensional model information usable to form an abutment tooth.

According to the present invention, the invisible portion in the image-capturing target site is of a shape formed by the surgical operation, and the shape is displayed as the three-dimensional image information side by side with the visible light image. Thus, the dental observation system may act as a surgical operation assistant or a surgical operation simulator.

In an embodiment according to the present invention, the dental observation device may further include a display switch operator switching the manner of display of the corresponding image.

According to the present invention, for example, data suitable to the surgical operation such as a cross-sectional view, volume data, numerical data or the like is displayed as the corresponding image.

In an embodiment according to the present invention, in the case of the root canal treatment or implant surgical operation, the display portion may display at least one piece of dental care data among a measured root canal length value, a shaving torque value and a shaving rotation rate instead of, or in addition to, the corresponding image.

According to the present invention, for example, more precise surgical operation is performed while the dental care data such as the surgical operation content in the past or the like is checked.

In an embodiment according to the present invention, the display portion may be a head-mountable display portion mountable on a head of an operation worker. the display portion may be a dental microscope held by a support arm extending from a side portion of a dental care device such that the position of the three-dimensional camera is changeable.

According to the present invention, the operation worker may perform the surgical operation by use of a device having more suitable specifications more in accordance with the surgical operation content or preference.

In an embodiment according to the present invention, the three-dimensional camera may include a blur prevention mechanism preventing a blur.

According to the present invention, the operation worker may perform the surgical operation while checking a clearer visible image.

In an embodiment according to the present invention, the three-dimensional camera may include a mirror image reversal mechanism performing mirror image reversal on the visible light image.

According to the present invention, the operation worker may perform the surgical operation while checking the mirror-reversed visible light image. Such a manner of performing the surgical operation is similar to the manner of performing the surgical operation while checking a dental mirror, to which the operation worker is accustomed.

The present invention is also directed to a dental observation device including a three-dimensional camera; a storage; an image-capturing direction detector; a display; and a processor. The three-dimensional camera performs three-dimensional image capturing of a visible light image of a desired image-capturing site in an oral cavity region. The storage stores three-dimensional image information on the oral cavity region acquired in advance. The image-capturing direction detector detects an image-capturing direction of the three-dimensional camera for the image-capturing site. The processor processes the three-dimensional image information on the basis of the image-capturing direction detected by the image-capturing direction detector to generate a corresponding image corresponding to the image-capturing site in a predetermined direction, and causes the display to display the visible light image captured by the three-dimensional camera and the corresponding image side by side.

In an embodiment according to the present invention, the processor may cause the display to display three-dimensionally, based on left/right parallax, the visible light image of the image-capturing site obtained as a result of three-dimensional observation, and to display, two-dimensionally, the corresponding image as being viewed in a direction parallel to the image-capturing direction and at the same angle around the image-capturing direction as that of the visible light image.

In an embodiment according to the present invention, the three-dimensional image information may represent any one of a three-dimensional x-ray image acquired by an x-ray CT image-capturing device, a nuclear magnetic resonance image acquired by a nuclear magnetic resonance image-capturing device, an ultrasonic three-dimensional image acquired by an ultrasonic diagnostic image-capturing device, and an optical interference three-dimensional image acquired by an optical interference tomographic image-capturing device.

In an embodiment according to the present invention, based on the three-dimensional image information, the processor may cause the display to display a cross-sectional image in a direction based on the image-capturing direction, the cross-sectional view being displayed as the corresponding image.

In an embodiment according to the present invention, the processor may accept an cross-section adjustment operation of adjusting a cross-sectional position in a direction based on the image-capturing direction of the cross-sectional image.

Advantageous Effect of the Invention

The present invention provides a dental observation device and a method for displaying a dental image with which in the state where the visible light image of a desired image-capturing site in an oral cavity region captured by a three-dimensional camera and three-dimensional image information on the desired image-capturing site in the oral cavity region acquired in advance are not displayed in an overlapping manner, an invisible portion of the visible light image is easily recognized.

BRIEF DESCRIPTION OF DRAWINGS

FIG. 3 shows a display screen.
FIGS. 4A to 4C show parallax images.
FIGS. 8A to 8F show the subordinate image display adjustment.
FIGS. 11A and 11B show formation of an abutment tooth for a tooth.
FIGS. 12A to 12E show a case where a tooth is observed in different directions.
FIGS. 13A to 13C show image-capturing directions for teeth.

DESCRIPTION OF EMBODIMENTS

Hereinafter, a dental care system 1 according to the present invention will be described with reference to FIG. 1 through FIGS. 11A and 11B.

Figure 1:
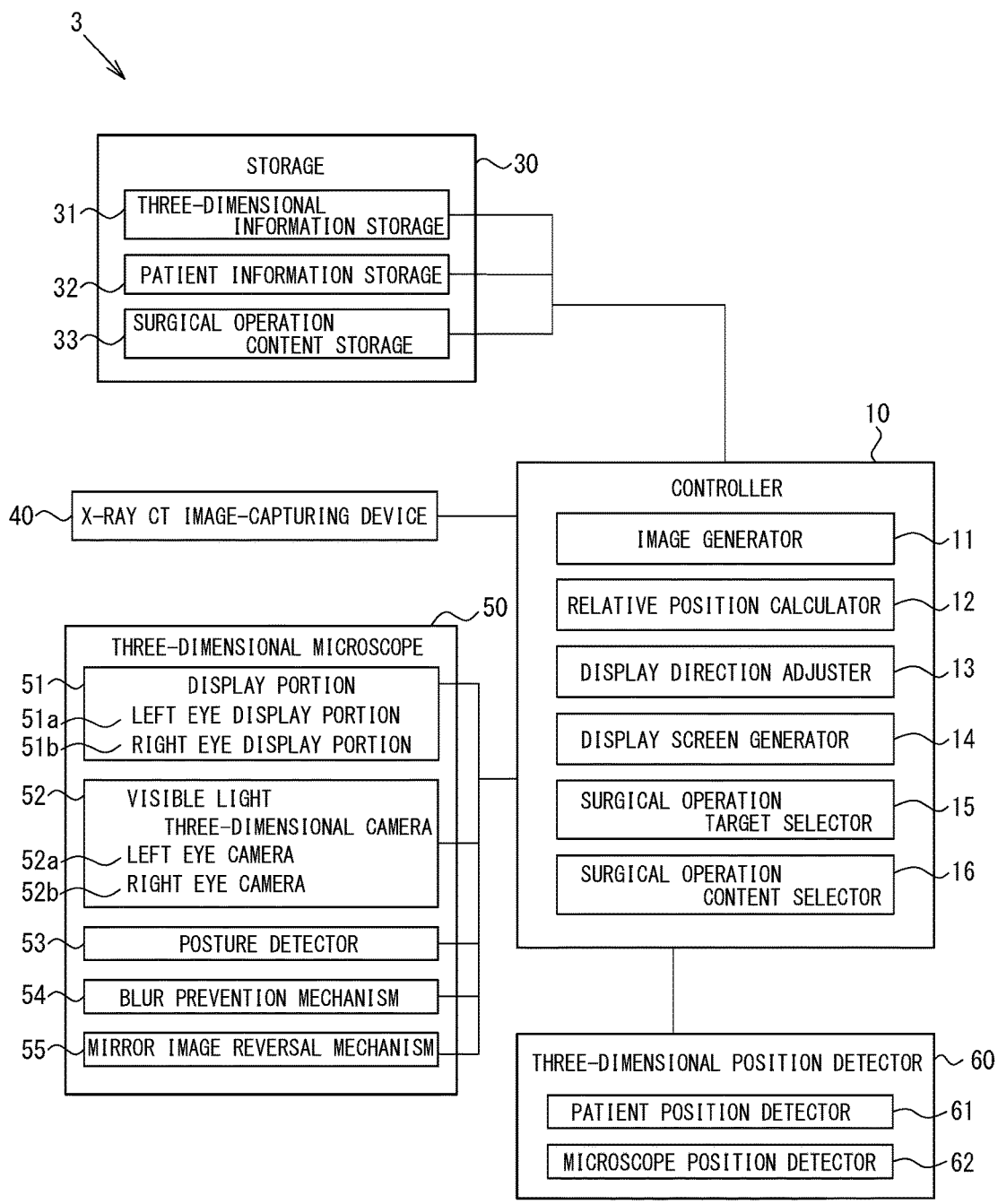
FIG. 1 is a block diagram of an observation system.
Figure 2:
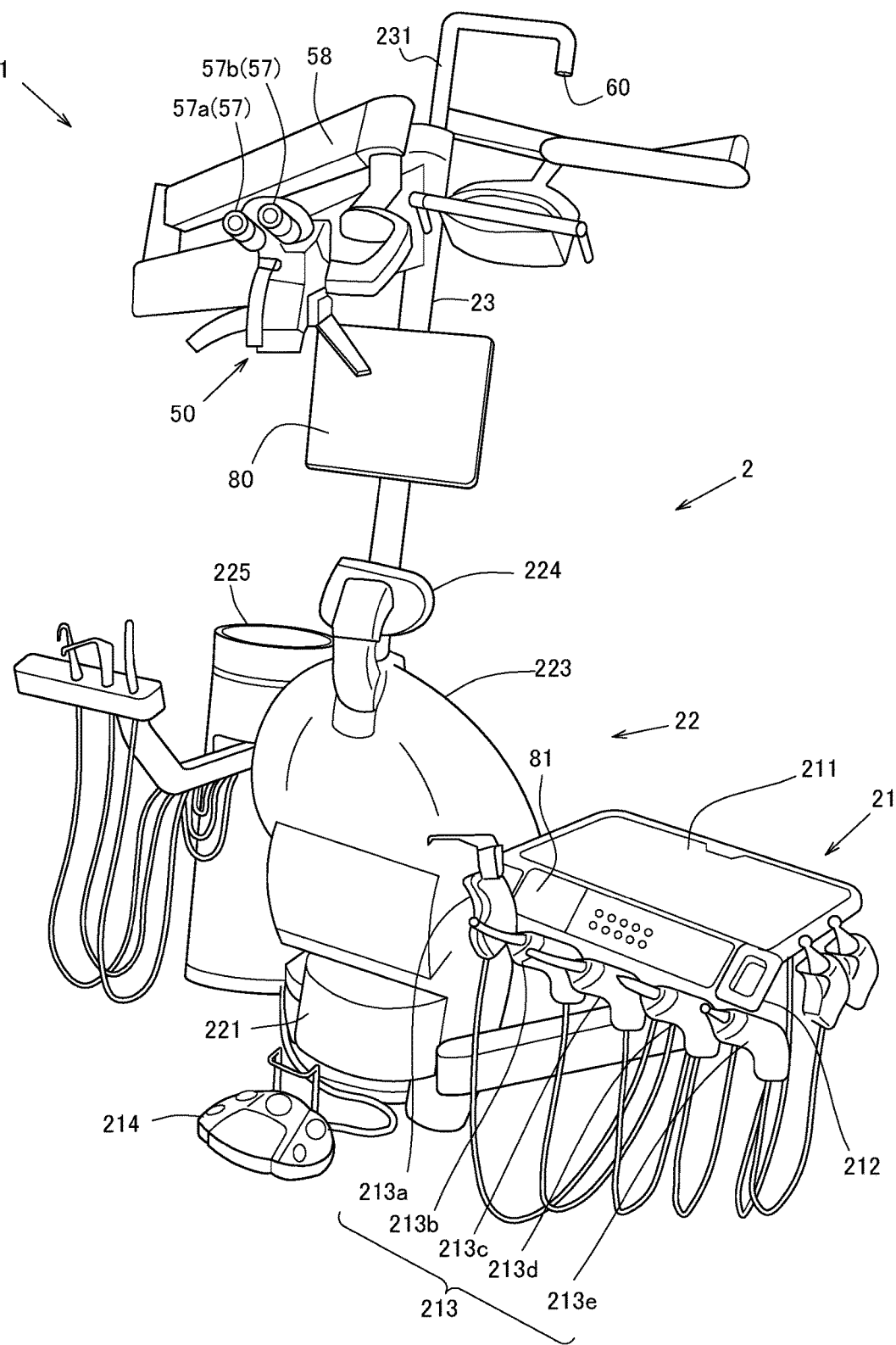
FIG. 2 is a schematic isometric view of a dental care system.
Figure 5:
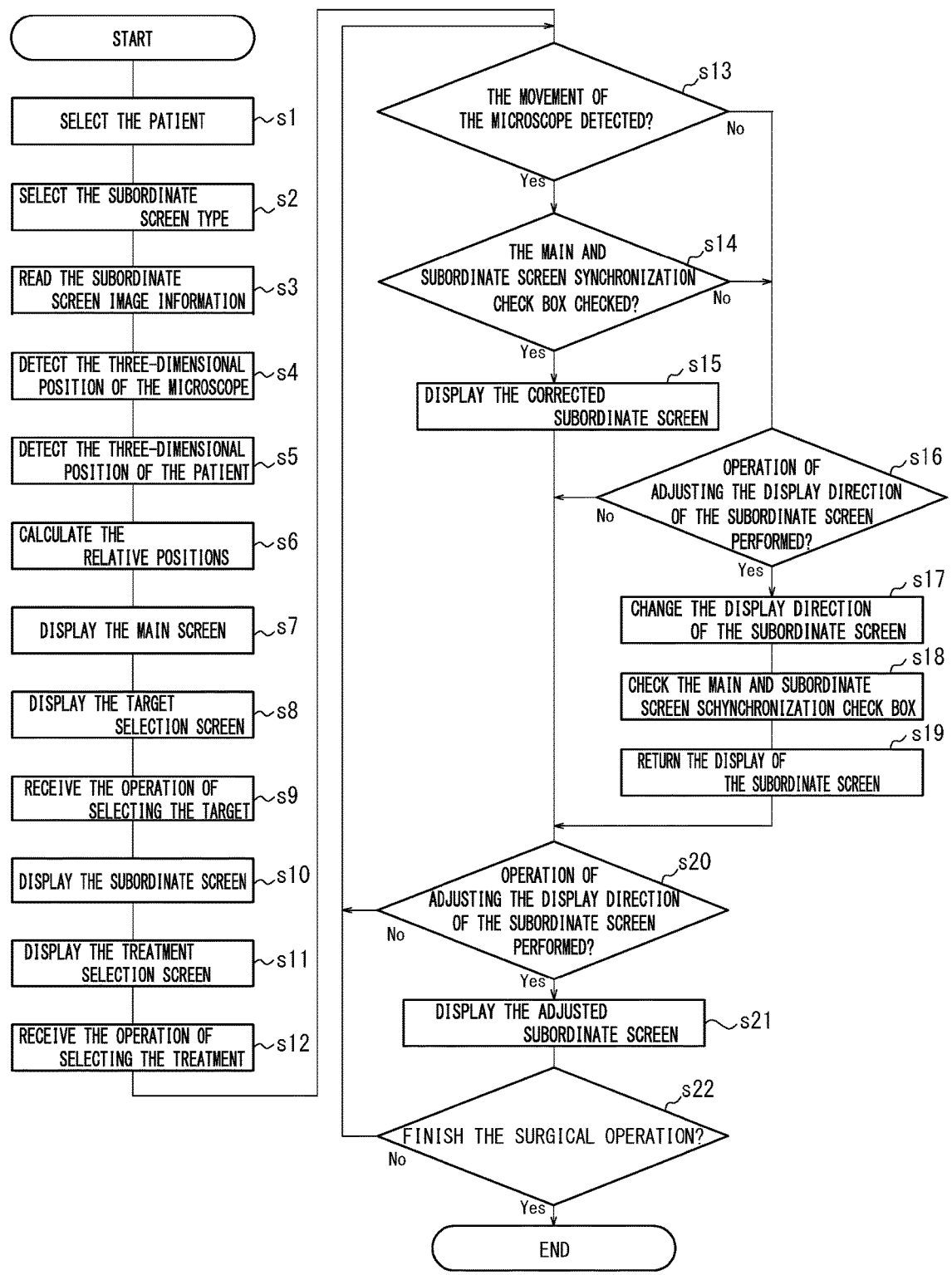
FIG. 5 is a flowchart of dental care.

FIG. 1 is a block diagram of an observation system 3 corresponding to the dental observation device. FIG. 2 is a schematic isometric view of the dental care system 1. FIG. 3 shows a display screen 100. FIGS. 4A to 4C show parallax images Sa and Sb in an image display portion 110. FIG. 5 is a flowchart of dental care. The dental observation device may be referred to as a "dental imager" or a "dental scope".

In the description of the embodiments, the term "image-capturing direction" will be used. The "image-capturing direction" may encompass a direction along a direction of incidence of light entering a visible light three-dimensional camera 52 (may be considered as a direction of the line of sight; specifically, is an axial direction of an optical axis of an objective lens) or an image-capturing angular direction around the direction of incidence of the light entering the visible light three-dimensional camera 52 (namely, a circumferential direction around the direction of incidence of the light). The image-capturing angular direction is defined by, for example, the pivoting angle of the visible light three-dimensional camera 52 around the axial direction of the optical axis of the objective lens. In the case where it is easier to understand if the image-capturing direction is described as only indicating the direction along the direction of incidence of light, the expression "image-capturing direction (direction of the line of sight)" may be used. In the case where it is easier to understand if the image-capturing direction is described as only indicating the image-capturing angular direction, the expression "image-capturing direction (circumferential direction)" may be used. In the case where there is no need to distinguish the direction along the direction of incidence of light and the image-capturing angular direction, the term "image-capturing direction" may be used.

Figure 6A:
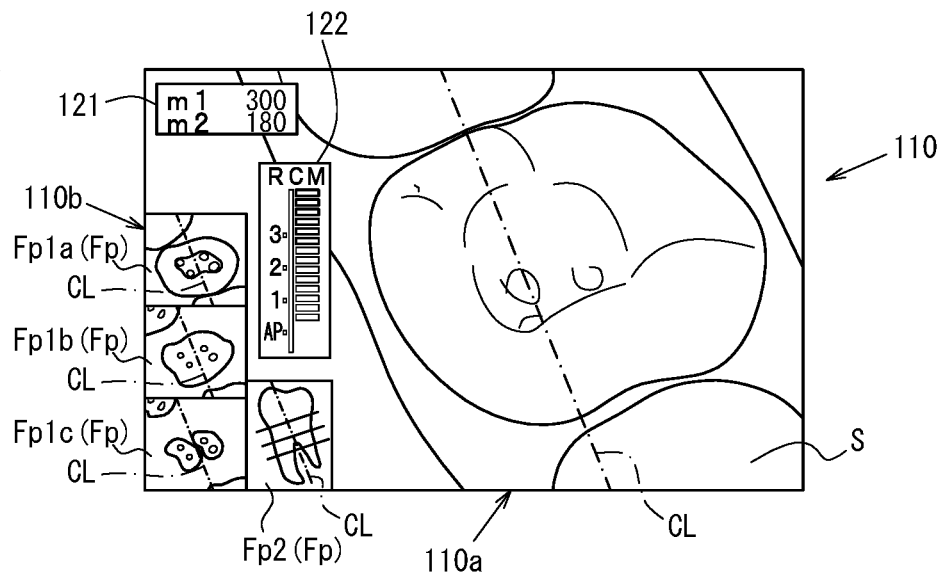
FIGS. 6A to 6C show an image display portion in the case where an image-capturing direction is changed.
Figure 6B:
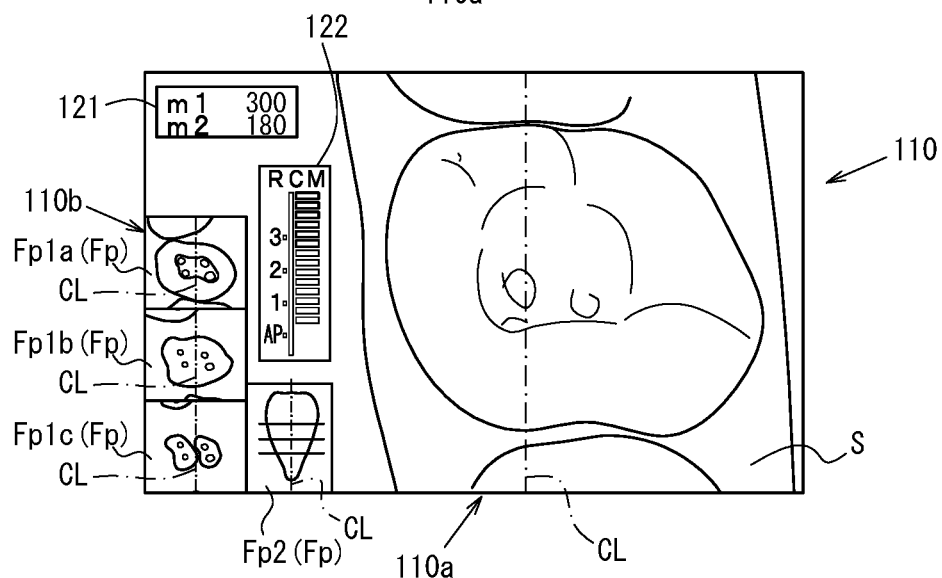
Figure 6C:
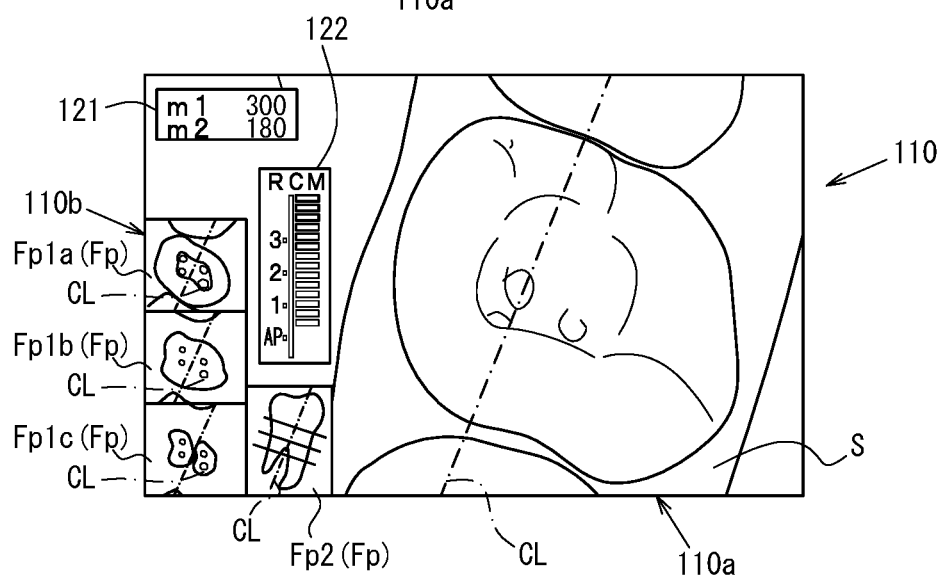
Figure 7A:
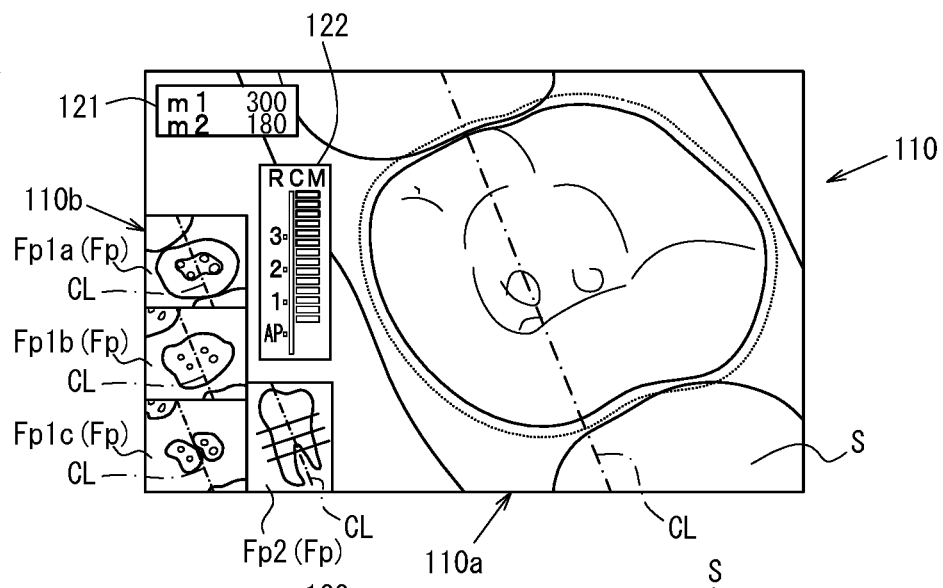
FIGS. 7A to 7C show the image display portion regarding subordinate image display adjustment.
Figure 7B:
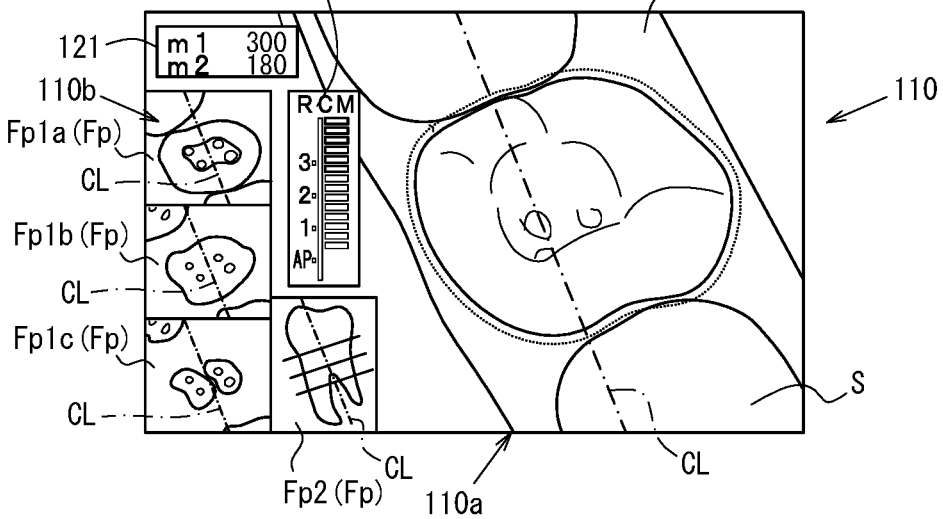
Figure 7C:
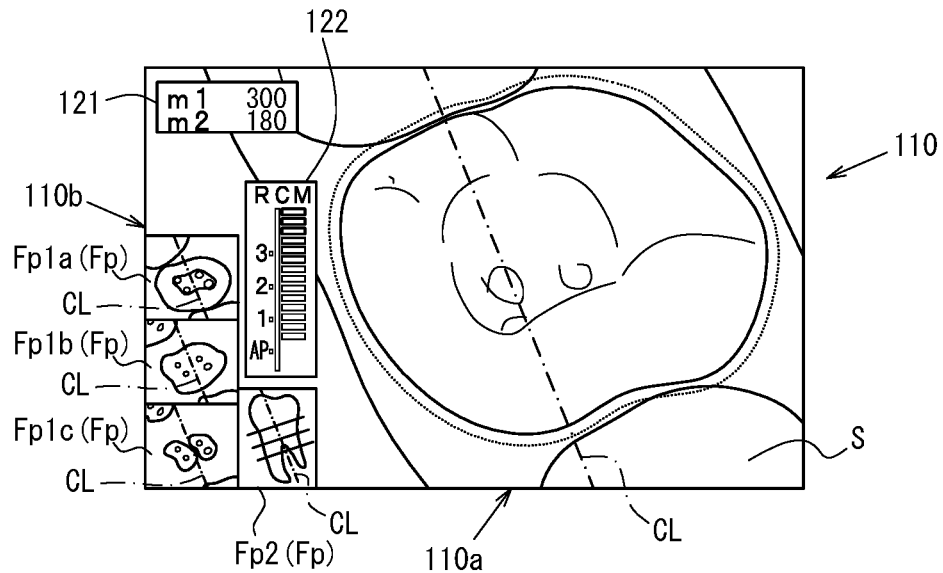

FIGS. 6A to 6C show the image display portion 110 in the case where the image-capturing direction (circumferential direction) is changed. FIGS. 7A to 7C show the image display portion 110 regarding subordinate image adjustment. FIGS. 8A to 8F show adjustment on a subordinate image display portion 110b in the image display portion 100. FIGS. 9A to 9D show the image display portion 110 regarding display switch of subordinate screens.

More specifically, FIG. 4A shows the image display portion 110 displaying the left parallax image Sa displayed in a left eye display portion 51a. FIG. 4B shows the image display portion 110 displaying the right parallax image Sb displayed in a right eye display portion 51b. FIG. 4C shows the image display portion 110 three-dimensionally displaying the three-dimensional captured image S. FIG. 4A and FIG. 4B each show, by the dashed line, the observation target three-dimensionally displayed.

FIG. 6A shows the image display portion 110 before the image-capturing direction (circumferential direction) is changed. FIG. 6B shows the image display portion 110 after the image-capturing direction (circumferential direction) is rotated clockwise by a predetermined angle. FIG. 6C shows the image display portion 110 after the image-capturing direction (circumferential direction) is further rotated clockwise by a predetermined angle.

FIG. 7A shows the image display portion 110 before the subordinate image display portion 110b is adjusted. FIG. 7B shows the image display portion 110 after the three-dimensional captured image S is adjusted to be smaller to increase the size of the subordinate image display portion 110b. FIG. 7C shows the image display portion 110 after the three-dimensional captured image S is adjusted to be larger to decrease the size of the subordinate image display portion 110b.

FIG. 8A shows the image display portion 110 three-dimensionally displaying the three-dimensional captured image S. FIG. 8B shows the image display portion 110 displaying the left parallax image Sa displayed in the left eye display portion 51a. FIG. 8C shows the image display portion 110 displaying the right parallax image Sb displayed in the right eye display portion 51b. FIG. 8D shows size adjustment on the subordinate image display portion 110b in the image display portion 110 three-dimensionally displaying the three-dimensional captured image S. FIG. 8E shows size adjustment on the subordinate image display portion 110b in the image display portion 110 displaying the left parallax image Sa displayed in the left eye display portion 51a. FIG. 8F shows size adjustment on the subordinate image display portion 110b in the image display portion 110 displaying the right parallax image Sb displayed in the right eye display portion 51b. FIG. 8B and FIG. 8C each show, by the dashed line, the observation target displayed three-dimensionally. In FIGS. 8A to 8F, a rotation rate display portion 121 and a root canal length display portion 122 are omitted.

Figure 9A:
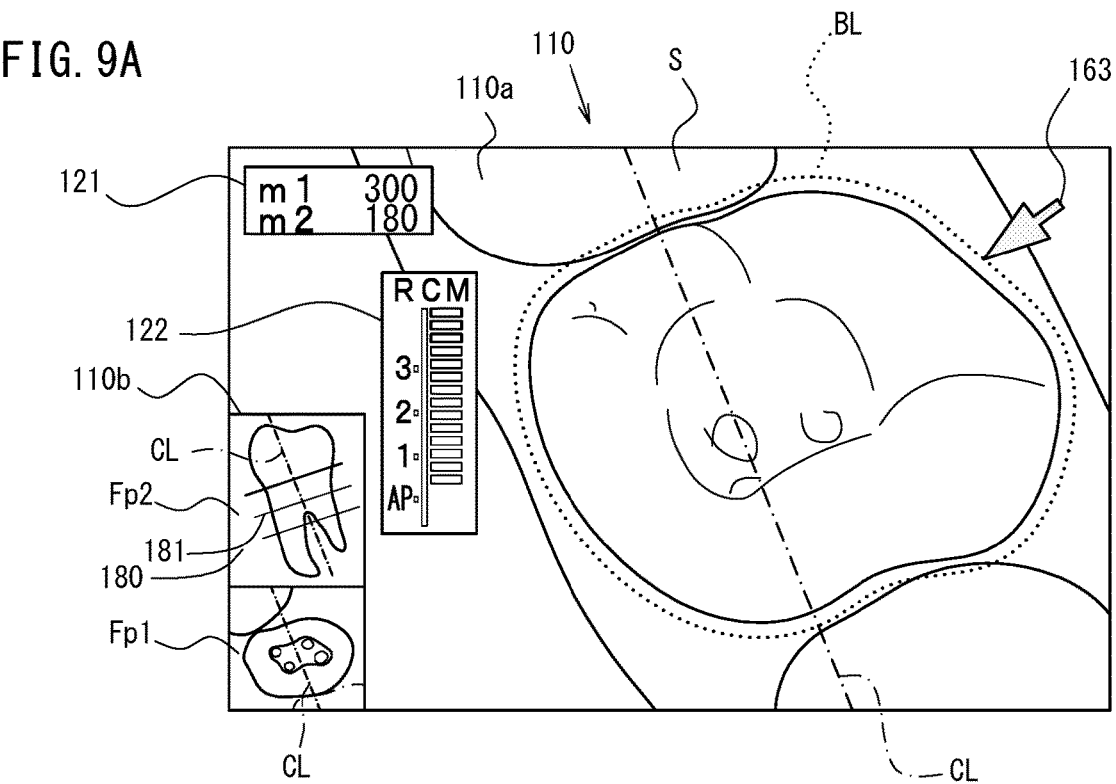
FIGS. 9A to 9D show the image display portion regarding display switch of subordinate screens.
Figure 9B:
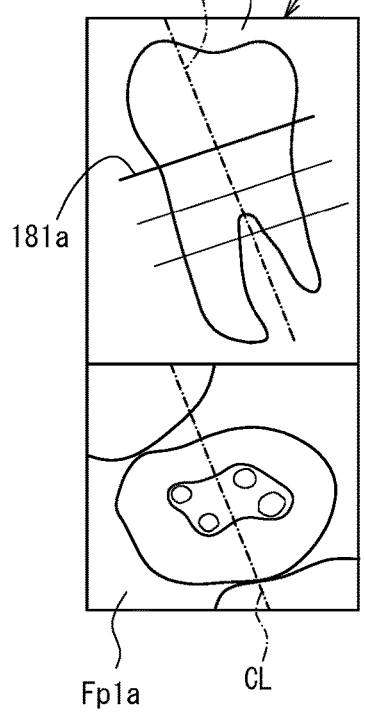
Figure 9C:
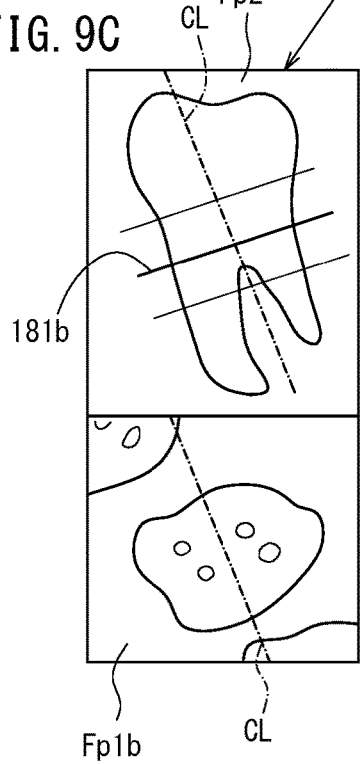
Figure 9D:
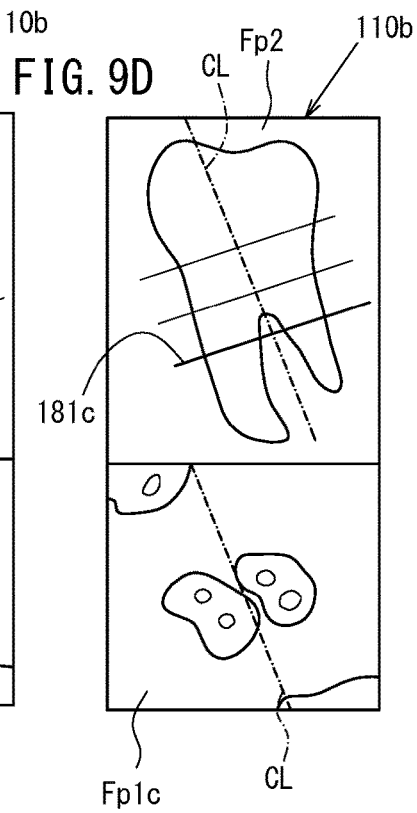
Figure 10A:
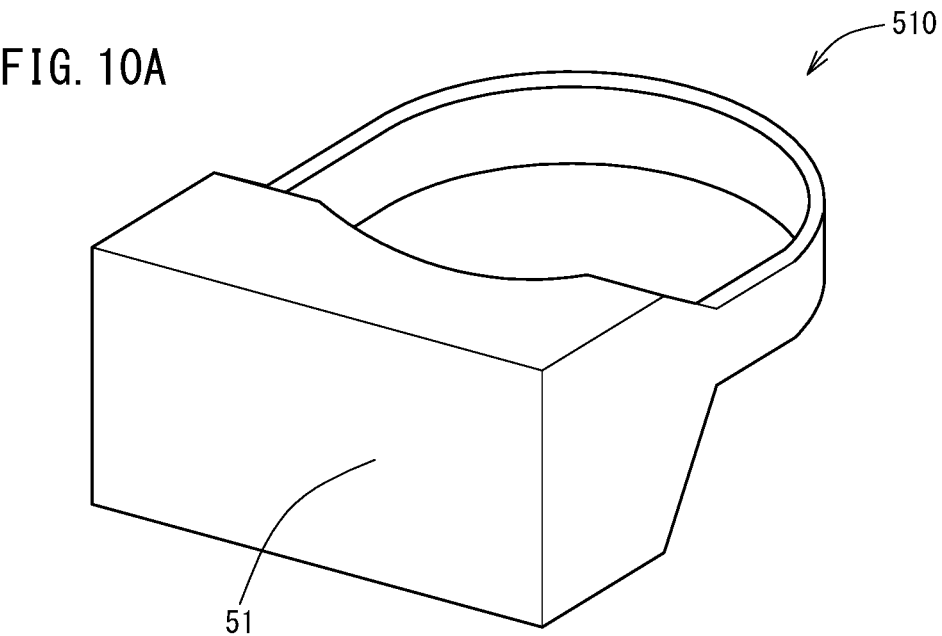
FIGS. 10A and 10B show displays.
Figure 10B:
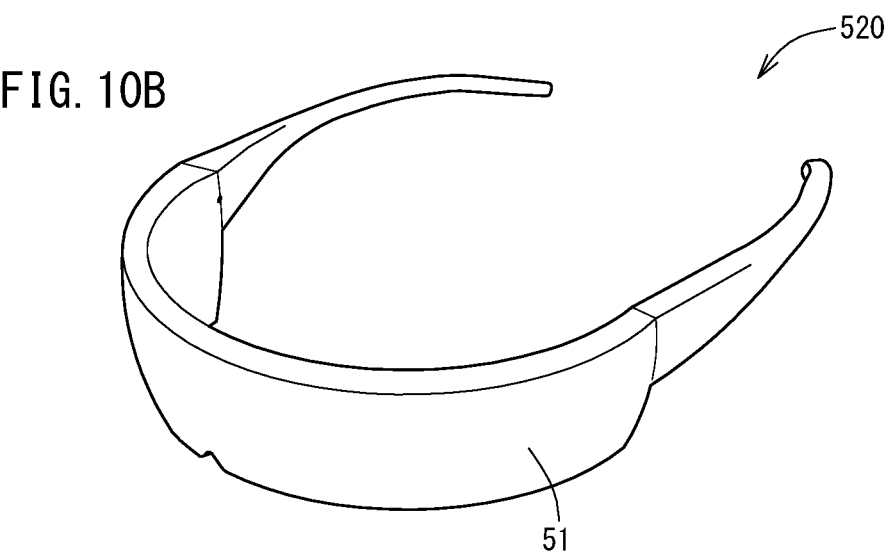

FIG. 9A shows the image display portion 110. FIG. 9B through FIG. 9D show a cross-sectional position view Fp2 and converted cross-sectional views Fp1 at different cross-sectional positions. FIGS. 10A and 10B show an HMD 510 and an HUD 520 (corresponding to the head mountable display portion) each acting as a display portion 51.

Referring to FIG. 2, the dental care system 1 includes a chair unit 2 and the observation system 3 (see FIG. 1) usable with a dental three-dimensional microscope 50 (dental microscope).

As shown in FIG. 2, the chair unit 2 includes a tool table 21 including dental care tools 213a through 213e, and a dental care table 22 on which a patient M as a surgical operation target may sit for a treatment.

The tool table 21 includes a table 211 pivotably attached to the dental care table 22 via an arm, and a tool holder 212 located to the front of the table 211. The tool table 21 further includes a dental care tool 213 (213a through 213e) detachably attached to the tool holder 212. The dental care tool 213 (213a through 213e) includes, for example, cutting tools such as an air turbine hand piece, a micromotor hand piece and the like, a scaler, a three-way syringe, a vacuum syringe and the like.

The dental care tool 213 is connected with a water supply source, an air supply source or an air absorber or the like to be driven. These mechanisms are known and will not be described in detail.

The tool table 21 also includes a foot controller 214 to which various operations are input. The mechanism of the foot controller 214 is known and will not be described in detail.

As shown in FIG. 2, the dental care table 22 on which the patient M may sit includes a seat attached to a base 221 so as to be elevated up and down, an inclinable back seat 223 connected to, and provided to the rear of, the seat, and an inclinable head rest 224 connected to a top end of the back seat 223. The dental care table 22 further includes a seat elevator, a back seat incliner, and a head rest incliner respectively controlling the seat, the back seat 223 and the head rest 224 to an optimal position in accordance with the state of the dental care. A hydraulic cylinder, an electric motor or the like controlled to be operated by the foot controller 214 is driven to drive the seat elevator, the back seat incliner and the head rest incliner.

The dental three-dimensional microscope 50 is supported by a support arm 58, the position of which is adjustable.

The dental care table 22 is provided with a spittoon 225 and a treatment stand pole 23. An arm 231 is branched from the middle of the treatment stand pole 23 attached to the spittoon 225, and is pivotably protrudes from the treatment stand pole 23. A three-dimensional position detector 60 of the observation system 3 (described below) is attached to a tip of the arm 231. The treatment stand pole 23 supports the dental three-dimensional microscope 50, which is movable up, down, leftward and rightward by the support arm 58.

FIG. 2 shows an example in which the dental three-dimensional microscope 50 is attached to the support arm 58 supported by the treatment stand pole 23 attached to the spittoon 225. The present invention is not limited to such a structure. The treatment stand pole may be attached to the ceiling, or a caster may be attached to a bottom portion of the treatment stand pole, so that the treatment stand pole is independently movable.

The spittoon 225 includes a water supply valve usable to supply water when, for example, the patient M is to wash the oral cavity, and a spit bowl. A connector (not shown) connected with an electric route, a hydraulic route or an air route provided in the chair unit 2 is provided to be in contact with the back or the abdomen of the patient M.

As shown in FIG. 1, the observation system 3 included in the dental care system 1 together with the chair unit 2 includes a controller 10, a storage 30, the dental three-dimensional microscope 50, and the three-dimensional position detector 60.

FIG. 1 shows an x-ray CT image-capturing device 40 as a component of the dental care system 1. The x-ray CT image-capturing device 40 is not indispensable for the present invention. Three-dimensional image data (three-dimensional image information) is necessary for the present invention, and it is sufficient that the three-dimensional image data is stored on the storage 30. According to the present invention, the three-dimensional image does not need to be an x-ray CT image, and may be three-dimensional image data acquired by a device capable of acquiring another type of three-dimensional image information.

The controller 10 includes a CPU, a ROM and a RAM; more specifically, the following functional components.

The controller 10 includes an image generator 11, a relative position calculator 12 corresponding to the image-capturing direction detector, a display direction adjuster 13 corresponding to the image processor, a display screen generator 14, a surgical operation target selector 15, and a surgical operation content selector 16. A specific mechanical element of each of the functional components is a processor or a circuit. Such a processor or circuit is supplied with a signal to provide the corresponding function. FIG. 1 shows an example in which the controller 10 is separate from the dental three-dimensional microscope 50. Alternatively, the controller 10 may be included in the dental three-dimensional microscope 50.

The image generator 11 generates various types of images. For example, the image generator 11 converts three-dimensional image information acquired by the x-ray CT image-capturing device 40 into two-dimensional image of a predetermined surface to generate a planar display-converted image Fp, and also generates a three-dimensional captured image S (corresponding to the visible light image) based on information captured by the visible light three-dimensional camera 52 corresponding to the three-dimensional camera.

The relative position calculator 12 calculates three-dimensional relative positions of the dental three-dimensional microscope 50 and the patient M, the three-dimensional positions of which have been detected by the three-dimensional position detector 60 (described below). The display direction adjuster 13 adjusts the display orientation in which the planar display-converted image Fp (corresponding to the corresponding image) to be displayed in the subordinate image display portion 110b (described below) based on the three-dimensional relative positions of the dental three-dimensional microscope 50 and the patient M detected by the relative position calculator 12. The planar display-converted image Fp is an image, in the three-dimensional captured image S, corresponding to an image-capturing site.

The display screen generator 14 generates image display that displays the three-dimensional captured image S or the planar display-converted image Fp generated by the image generator 11, or displays display screen 100 (FIG. 3) based on the planar display-converted image Fp, the display direction of which has been adjusted by the display direction adjuster 13.

The surgical operation target selector 15 selects a surgical operation target site corresponding to the image-capturing site. As shown by, for example, dotted line BrL in FIG. 3, the surgical operation target selector 15 selectively recognizes the surgical operation target site in an image displayed in the image display portion 110 of the display screen 10.

The surgical operation content selector 16 may select a content of the surgical operation for the surgical operation target site selected by the surgical operation target selector 15. The surgical operation content selector 16 may automatically display information useful for the surgical operation in a display manner appropriate to the surgical operation target site in accordance with the selected surgical operation content.

Referring to FIG. 3, in the case where, for example, a root canal treatment is selected, the surgical operation content selector 16 may display, on the display screen 100, a root canal length measurement image, a root canal cutting torque and a cutting rotation rate concurrently with the x-ray CT image. In the example shown in FIG. 3, the root canal length display portion 122 displays the root canal length measurement image, and the rotation rate display portion 121 displays the cutting rotation rate. A root canal length measurement image shows a measured root canal length value. The measured root canal length value is displayed as a value indicating a distance between a tip of a tool such as a file, a reamer or the like and the root apex.

The storage 30 includes an HDD, an SSD, a RAM or the like, and is connected with the controller 10. The storage 30 is controlled by the controller 10 such that various types of information may be stored on, or retrieved from, the storage 30. The storage 30 includes, for example, a three-dimensional information storage 31 (corresponding to the storage) storing three-dimensional image information on the surgical operation target site such as, for example, three-dimensional x-ray image information acquired by the x-ray CT image device 40, a patient information storage 32 storing at least information on the surgical operation such as, for example, the medical history or treatment information regarding the patient M, and a surgical operation content storage 33 storing, for example, the type of the surgical operation content performed in the oral cavity or the display manner suitable to the surgical operation content.

The three-dimensional information storage 31 may store, for example, a nuclear magnetic resonance image, an ultrasonic three-dimensional image, an optical interference tomographic image, three-dimensional scanning data acquired by a three-dimensional oral cavity scanner, three-dimensional image information on an implant, three-dimensional model information for forming an abutment tooth, or stl data thereon, instead of, or in addition to, the three-dimensional x-ray image.

The x-ray CT image-capturing device 40 may be a well-known dental or medical x-ray CT image-capturing device.

The x-ray CT image-capturing device 40 directs an x-ray cone beam toward a subject, and an x-ray detector swiveling around the subject detects an x-ray to acquire three-dimensional image information.

The x-ray CT image-capturing device 40 stores the acquired three-dimensional image information on the three-dimensional information storage 31 of the storage 30. Alternatively, the x-ray CT image-capturing device 40 may not be a component of the dental care system 1 or the observation system 3, and may be separately provided. Still alternatively, the x-ray CT image-capturing device 40 may not be provided, and merely the three-dimensional image information may be stored on the three-dimensional information storage 31 of the storage 30.

A device acquiring the three-dimensional image information may be a magnetic resonance image-capturing device (MRI) acquiring a nuclear magnetic resonance image, an ultrasonic diagnostic image-capturing device acquiring an ultrasonic three-dimensional image, an optical interference tomographic image-capturing device acquiring an optical interference three-dimensional image, a three-dimensional oral cavity scanner acquiring three-dimensional scanning data, or the like. Such a device may be provided instead of, or in addition to, the x-ray CT image-capturing device 40.

As shown in FIG. 1 and FIG. 2, the dental three-dimensional microscope 50 is a binocular type microscope that is widely used for dental diagnosis by an operation worker to observe a surgical operation target site. The dental three-dimensional microscope 50 includes the display 51 (51a and 51b) displaying the display screen 100 or the like for the view field of the operation worker, the visible light three-dimensional camera 52 (52a and 52b) capturing the three-dimensional captured image S to be displayed in a main image display portion 110a of the display screen 100, a posture detector 53 including a gyrosensor or the like and detecting a posture of the dental three-dimensional microscope 50, a blur prevention mechanism 54 absorbing the vibration of the visible three-dimensional camera 52 (52a and 52b) capturing the three-dimensional captured image S to prevent a blur of the captured image, a mirror image reversal mechanism 55 performing mirror image reversal of the three-dimensional captured image S captured by the visible three-dimensional camera 52 (52a and 52b), an illuminator illuminating the surgical operation target site, and an eye contact portion 57 (57a and 57b).

The mechanisms of the posture detector 53 including a gyrosensor or the like, the blur prevention mechanism 54 and the mirror image reversal mechanism 55 are known and will not be described in detail.

As shown in FIG. 2, the dental three-dimensional microscope 50 is supported by the support arm 58 so as to be movable up, down, leftward and rightward and rotatable. The dental three-dimensional microscope 50 includes cameras 52a and 52b on a plane directed toward the patient M and also the illuminator (not shown) distanced from the cameras 52a and 52b by a predetermined gap in a direction perpendicular to the cameras 52a and 52b. The illuminator includes an LED. The visible light three-dimensional camera 52 including the cameras 52a and 52b is a two-lens camera. Alternatively, the visible light three-dimensional camera 52 may be a single-lens camera capable of capturing a three-dimensional image.

As shown in FIG. 2, the dental three-dimensional microscope 50 includes the eye contact portion 57 (57a and 57b) on a surface on the side of the operation worker. The operation worker may look into the eye contact portion 57 to visually recognize the display portion 51 (51a and 51b) inside.

This will be described in more detail. The visible light three-dimensional camera 52, of the dental three-dimensional microscope 50, provided on the side of the patient M includes the left eye camera 52a capturing the left parallax image Sa from the left of the observation target and the right eye camera 52b capturing an the right parallax image Sb from the right of the observation target. The left eye camera 52a and the right eye camera 52b are located with an interval corresponding to the interval between the left eye and the right eye of a human.

The display portion 51 located inside the dental three-dimensional microscope 50 includes the left eye display portion 51a displaying the left parallax image Sa captured by the left eye camera 52a and the right eye display portion 51b displaying the right parallax image Sb captured by the right eye camera 52b.

The eye contact portion 57, of the dental three-dimensional microscope 50, provided on the side of the operation worker includes the left eye contact portion 57a collimating the left eye display portion 51a displaying the left parallax image Sa captured by the left eye camera 52a and the right eye contact portion 57b collimating the right eye display portion 51b displaying the right parallax image Sb captured by the right eye camera 52b. The left eye contact portion 57a is to be in contact with the left eye of the operation worker, and the right eye contact portion 57b is to be in contact with the right eye of the operation worker. The left eye contact portion 57a and the right eye contact portion 57b are located with an interval corresponding to the interval between the left eye and the right eye of a human.

FIG. 2 shows a structure in which the operation worker may look into the eye contact portion 57 located on the side of the patient M to look at the display portion 51 (51a and 51b) provided inside the dental three-dimensional microscope 50. Alternatively, the display portion 51 (51a and 51b) may be provided separately from the dental three-dimensional microscope 50. For example, the display portion 51 (51a and 51b) may be included in a head mounted display (HMD) 510 shown in FIG. 10A or an eye-glasses type head-up display shown in FIG. 10B. The display portion may include a display monitor 80 included in the chair unit 2 shown in FIG. 2 or a monitor 81 provided in the tool table 21.

The HMD 510 attachable to the head of the operation worker includes the display portion 51 (51a and 51b) corresponding to the field of view. The HMD 510 receives, from the controller 10 in a contactless manner, and displays the three-dimensional captured image S or the planar display-converted image Fp generated by the image generator 11 or the display screen information such as the display screen 100 or the like generated by the display screen generator 14 based on a planar display-converted image Fp, the display direction of which has been adjusted by the display direction adjuster 13.

The HUD 520 wearable by the operation worker like eye glasses operates as follows. A projector (not shown) projecting an image onto a front eye-glass portion in a semi-transparent manner acts as the display portion 51 (51a and 51b). Thus, the HUD 520 receives, from the controller 10 in a contactless manner, and displays the display screen information such as the display screen 100 or the like generated by the display screen generator 14 in a semi-transparent manner.

The HMD 510 or the HUD 520 may include the visible light three-dimensional camera 52 (52a and 52b) to act as the dental three-dimensional microscope 50. The mirror image reversal mechanism 55 provided in the dental three-dimensional microscope 50 may be provided in the controller 10. The controller 10 may include, instead of the blur prevention mechanism 54, a processor that performs image processing on a three-dimensional captured image S that is blurred to provide an image that is not blurred.

The three-dimensional position detector 60 includes a patient position detector 61 detecting a three-dimensional position of the patient M and a microscope position detector 62 detecting a three-dimensional position of the dental three-dimensional microscope 50. The patient position detector 61 and the microscope position detector 62 may each be structured to detect the three-dimensional position by collimating a plurality of position detection markers (not shown) provided in a detection target, the three-dimensional position of which is to be detected. Alternatively, the patient position detector 61 and the microscope position detector 62 may each include an image recognition/position detection mechanism that detects the three-dimensional position by image recognition.

Still alternatively, the patient position detector 61 and the microscope position detector 62 may each include an infrared sensor detector. In this case, a reflective plate is provided on the detection target, and the infrared sensor detector directs laser light toward the reflective plate and measures the reflected light to measure the three-dimensional position. Alternatively, the infrared sensor detector detects the position by use of infrared light reflected by a reflection portion. The patient position detector 61 and the microscope position detector 62 may each include a radio wave detector that detects the position based on a radio wave transmitted from a radio wave transmitter.

The patient position detector 61 and the microscope position detector 62 may include three-dimensional position detection mechanisms that detect the three-dimensional positions by different detection methods from each other.

Now, with reference to FIG. 3, the display screen 100 to be displayed in the display portion 51 (51a and 51b) in the observation system 3 having the above-described structure will be described.

The display screen 100 displays the image display portion 110 corresponding to the display portion, a patient information display portion 130 displaying patient information, a subordinate screen information display portion 140 displaying information on the three-dimensional image information to be displayed in the subordinate image display portion 110b, and an operator 150 receiving various types of operation.

The image display portion 110 includes the main image display portion 110a displaying the three-dimensional captured image S captured by the dental three-dimensional microscope 50 and the subordinate image display portion 110b (corresponding to the corresponding image display region) displaying the planar display-converted image Fp based on the three-dimensional image information on the surgical operation target site displayed in the main image display portion 110a. The image display portion 110 displays the main image display portion 110a and the subordinate image display portion 110b side by side, such that the subordinate image display portion 110b does not overlap a main portion of the surgical operation target site in the three-dimensional captured image S on the main image display portion 110a. The image display portion 110 displays the rotation rate display portion 121 and the root canal length display portion 122 in addition to the main image display portion 110a and the subordinate image display portion 110b.

As shown in the figure, the root canal length display portion 122 may display the root canal length measurement image. For example, a root canal length measurement signal may be input from a root canal length measurement device (not shown) built in the dental care system 1 to the controller 10, or a root canal length measurement signal may be input from a root canal length measurement device provided outer to the dental care system 1 to the controller 10, and the measurement signal and the root canal length measurement image are associated with each other. Specifically, the position, of the tip of the tool such as the file, the reamer or the like inserted into the root canal, with respect to the root apex is made displayable. For example, as shown in the figure, the root apex is represented by "AP", the position of the tip of the tool is displayed with emitted light in the form of a segment, and the distance to the root apex is represented by a numerical value.

The planar display-converted image Fp in the subordinate image display portion 110b shown in FIG. 3 includes a converted cross-sectional view Fp1 showing the surgical operation target site and a cross-sectional position view Fp2 showing a cross-sectional position of the cross-sectional view. The converted cross-sectional view Fp1 shows converted cross-sectional views Fp1a through Fp1c at different cross-sectional positions.

As shown in FIG. 3, FIGS. 4A to 4C and FIGS. 6A to 6C through FIGS. 9A to 9D, the three-dimensional display captured image S, the converted cross-sectional view Fp1 and the cross-sectional position view Fp2 are displayed such that collimation axes CL thereof are parallel to each other. The collimation axes CL may, or may not, be displayed.

As described above, the three-dimensional captured image S and the converted cross-sectional view Fp1 are displayed with the same image-capturing direction (direction of the line of sight) and the same angle around the image-capturing direction (direction of the line of sight), namely, the same image-capturing direction (circumferential direction).

Herein, the angle in the circumferential direction of each of the three-dimensional captured image S and the converted cross-sectional view Fp1 in a display state with respect to the image-capturing direction (circumferential direction) will be referred to as a "circumferential direction display angle", and the display of such a image at the circumferential direction display angle will be referred to as a "circumferential direction display". The three-dimensional captured image S and the converted cross-sectional view Fp1 match each other in the circumferential direction display angle and the circumferential direction display.

Namely, in this example, the three-dimensional captured image S and the converted cross-sectional view Fp1 are displayed such that the collimation axes CL thereof are parallel to each other. As a result, three-dimensional captured image S and the converted cross-sectional view Fp1 are displayed two-dimensionally in the state where the direction of the line of sight is the same for the same site. The cross-sectional position view Fp2 is a side view of a volume image of a three-dimensional x-ray image of a designated tooth. The cross-sectional position view Fp2 is an image parallel to the direction of the line of sight, more specifically, a volume image in a direction of a tooth axis. In this example, the cross-sectional position view Fp2 is the side view of the volume image. Alternatively, a cross-sectional image may be displayed instead of the volume image.

The cross-sectional position view Fp2 displays a plurality of straight lines with a predetermined interval in an axial direction (display position lines 181). The plurality of straight lines 181 show the cross-sectional positions of the cross-sectional views shown in the converted cross-sectional view Fp1. The converted cross-sectional view Fp1 shows the converted cross-sectional views Fp1a, Fp1b and Fp1c at different depths along the collimation axis CL. In the case where the tooth is cut by a cutting tool, the surgical operation may be performed while it is drawn how the cross-section of the root canal or the like is changed.

With reference to FIGS. 4A to 4C, the three-dimensional captured image S and the planar display-converted image Fp in the image display portion 110 including the main image display portion 110a and the subordinate image display portion 110b will be described in detail.

The image display portion 110 includes the left eye display portion 51a and the right eye display portion 51b.

As shown in FIG. 4C, the three-dimensional captured image S is displayed three-dimensionally in the main image display portion 110a as follows. The left parallax image Sa (see FIG. 4A) captured by the left eye camera 52a and displayed in the left eye display portion 51a is collimated by the operation worker with his/her left eye via the left eye contact portion 57a. The right parallax image Sb (see FIG. 4B) captured by the right eye camera 52b and displayed in the right eye display portion 51b is collimated by the operation worker with his/her right eye via the right eye contact portion 57b. Thus, the operation worker visually recognizes the three-dimensional captured image S three-dimensionally.

This will be described in more detail. The left parallax image Sa captured by the left eye camera 52a and displayed in the left eye display portion 51a is conceptually displayed, for example, to the left of the three-dimensional image represented by the dashed line in FIG. 4A. The right parallax image Sb captured by the right eye camera 52b and displayed in the right eye display portion Sib is conceptually displayed, for example, to the right of the three-dimensional image represented by the dashed line in FIG. 4B. The left parallax image Sa and the right parallax image Sb represent how an image is viewed differently by the left eye and by the right eye (this difference is referred to as "parallax"). The left parallax image Sa and the right parallax image Sb are collimated by the left eye and the right eye independently from each other. In this manner, the operation worker visually recognize the three-dimensional captured image S three-dimensionally.

The distance between the pupils of both eyes is about 60 mm to about 70 mm, and is about 62 mm to about 64 mm on average, although varying in accordance with the gender or individually. Therefore, the left eye and the right eye have an angular difference when viewing the same object. Such an angular difference in the direction of viewing is referred to as the "parallax (binocular parallax)".

The left parallax image Sa and the right parallax image Sb, which have such a parallax, may both be displayed at positions represented by the dashed lines in FIG. 4A and FIG. 4B. The parallax between the left parallax image Sa and the right parallax image Sb does not need to be exactly the same angle as the binocular parallax, and may have a slight angular difference from the binocular parallax as long as there is a difference between the case where the object is viewed by the left eye and the case where the object is viewed by the right eye. This is also applicable to FIGS. 8A to 8F referred to below.

The left eye display portion 51a and the right eye display portion 51b are connected with, or are on an optical path of, an optical component by which the left parallax image Sa is in the field of vision of the left eye and the right parallax image Sb is in the field of vision of the right eye. With such a structure, the left parallax image Sa and the right parallax image Sb are viewed by the operation worker, or in more detail, are recognized in the brain of the operation worker as follows: the left parallax image Sa and the right parallax image Sb are not two divided left and right images but are combined three-dimensionally as one three-dimensional captured image S shown in FIG. 4C.

Mechanically, the main image display portion 110a individually displays the left parallax image Sa and the right parallax image Sb shown in FIG. 4A and FIG. 4B. However, the brain of the operation worker recognizes the left parallax image Sa and the right parallax image Sb as the three-dimensional captured image S shown in FIG. 4C. As a result, the brain of the operation worker recognizes the image display portion 110 in the state shown in FIG. 3. As can be seen, an image like the three-dimensional captured image S, which is recognized three-dimensionally in the brain, may be considered as a subjective three-dimensional captured image, and an image display portion displaying such a subjective three-dimensional captured image may be considered as a subjective image display portion.

The left parallax image Sa and the right parallax image Sb may show the surgical operation target site at different positions. In addition, in the case where the visible light three-dimensional camera 52 and the surgical operation target site have a certain positional relationship, the left parallax image Sa and the right parallax image Sb may show the surgical operation target site with different sizes or with different sizes and at different positions.

By contrast, the planar display-converted image Fp displayed in the subordinate image display portion 110b are at the same position and with the same size in the left eye display portion 51a and the right eye display portion 51b. Therefore, even if the left eye display portion 51a and the right eye display portion 51b are collimated respectively with the left eye and the right eye independently, the operation worker visually recognizes the planar display-converted image Fp two-dimensionally. The planar display-converted image Fp is displayed as a common image to the left and the right eyes with no left/right parallax in the left eye display portion 51a and the right eye display portion 51b.

As described above, the three-dimensional captured image S displayed three-dimensionally in the main image display portion 110a, and the planar display-converted image Fp displayed in the subordinate image display portion 110b, are different from each other in the relative positions of the surgical operation target site in the left parallax image Sa and the right parallax image Sb and the surgical operation target site displayed in the planar display-converted image Fp displayed two-dimensionally. The left parallax image Sa displayed in the left eye display portion 51a and the right parallax image Sb displayed in the right eye display portion 51b are different in the position or the size.

The patient information display portion 130 displaying the patient information displays the patient number, name, gender, age and the like of the patient M in a bottom portion of the image display portion 110 on the display screen 100.

The subordinate screen information display portion 140 displaying information on the three-dimensional image information to be displayed in the subordinate image display portion 110b displays the type or the data management number of the three-dimensional image information, base on which the planar display-converted image Fp of the surgical operation target site displayed in the subordinate image display portion 110b is to be generated. The type or the data management number is displayed in a bottom portion of the subordinate image display portion 110b on the display screen 100.

The operator 150 receiving various operations is displayed in a right portion of the display screen 100. The operator 150 includes, from top to bottom, a subordinate screen automatic adjustment operation button 151, a subordinate screen movement adjustment operation button 152, a subordinate screen size adjustment operation button 153, a subordinate screen display site change operation button 154, a subordinate screen display manner change operation button 155, a subordinate screen display direction change operation button 156, a subordinate screen display data change operation button 157, a main and subordinate screen synchronization check box 158, a surgical operation target selection operation button 159, a surgical operation content selection operation button 160, a patient change operation button 161, and a calibration operation button 162.

The subordinate screen automatic adjustment operation button 151 issues an instruction to automatically adjust, for example, at least one of the size and the position of the subordinate image display portion 110b displaying the planar display-converted image Fp, the rotation rate display portion 121 or the root canal length display portion 122 with respect to the main image display portion 110a. The instruction is issued when the image-capturing direction of the dental three-dimensional microscope 50 is changed, or in accordance with the surgical operation content.

The subordinate screen movement adjustment operation button 152 corresponding to the region adjuster is pressed to manually adjust the position of the subordinate image display portion 110b displaying the planar display-converted image Fp, the rotation rate display portion 121 or the root canal length display portion 122 with respect to the main image display portion 110a.

The subordinate screen size adjustment operation button 153 corresponding to the region adjuster is pressed to manually adjust the size of the subordinate image display portion 110b displaying the planar display-converted image Fp, the rotation rate display portion 121 or the root canal length display portion 122 with respect to the main image display portion 110a.

The subordinate screen display site change operation button 154 is pressed to change the cross-sectional position of the cross-sectional view of the surgical operation target site to be displayed in the subordinate image display portion 110b as the planar display-converted image Fp. The subordinate screen display site change operation button 154 is pressed to display, in the subordinate image display portion 110b, the tomographic images of the converted cross-sectional views Fp1a, Fp1b and Fp1c at different cross-sectional positions.

The subordinate screen display manner change operation button 155 corresponding to the display switch operator is pressed to change the display manner of the planar display-converted image Fp to be displayed in the subordinate image display portion 110b such that, for example, an external view, a horizontal cross-sectional view, a vertical cross-sectional view, or a frame view is to be displayed. The subordinate screen display manner change operation button 155 is also pressed to display the patient information on the patient M instead of the planar display-converted image Fp.

The subordinate screen display direction change operation button 156 corresponding to the display direction change operator is pressed to change the display manner of the planar display-converted image Fp to be displayed on the subordinate image display portion 110b.

The subordinate screen display data change operation button 157 is pressed to change the type of the three-dimensional image information on the surgical operation target site, based on which the planar display-converted image Fp to be displayed in the subordinate image display portion 110b is to be generated.

The main and subordinate screen synchronization check box 158 corresponding to the display direction reset operator issues an instruction to change the display direction, the angle around the image-capturing direction (direction of the line of sight), and the magnification ratio of the planar display-converted image Fp to be displayed on the subordinate image display portion 110b in synchronization with each other. The instruction is issued when the image-capturing direction (direction of the line of sight), the angle around the image-capturing direction (direction of the line of sight), namely, the image-capturing direction (circumferential direction), or the magnification ratio of the dental three-dimensional microscope 50 is changed.

The surgical operation target selection operation button 159 is pressed to select the site to be the surgical operation target in the three-dimensional captured image S to be displayed in the main image display portion 110a.

The surgical operation content selection operation button 160 is pressed to select the surgical operation content.

The patient change operation button 161 is pressed to change the patient information from the information on the patient M who has been subjected to the surgical operation when the surgical operation is to be performed on a different patient M.

The calibration operation button 162 is pressed to detect the three-dimensional relative positions of the dental three-dimensional microscope 50 and the patient M or to re-detect the three-dimensional relative positions of the dental three-dimensional microscope 50 and the patient M during the surgical operation.

As shown in FIG. 3, the display screen 100 structured as described above displays a cursor 163 represented by the arrow. The cursor 163 is operable by the foot controller 214 being stepped on, a gesture operation, a touch panel operation or the like.

With reference to the flowchart in FIG. 5, a dental care method and an observation method (display manner of a dental image) using the dental care system 1 including the observation system 3 structured as described above will be described.

First, the operation worker presses the patient change operation button 161 on the display screen 100 generated by the display screen generator 14 and displayed on the display portion 51 (51a and 51b) to select the patient M who is to be subjected to the surgical operation (step S1). When the patient M is selected, the controller 10 retrieves the patient information stored on the patient information storage 32 of the storage 30 and displays the patient information on the patient information display portion 130.

Next, the operation worker presses the subordinate screen display data change operation button 157 to select the type of the three-dimensional image information on which the planar display-converted image Fp to be displayed in the subordinate image display portion 110*b* is to be generated (step s2). When the type of the three-dimensional image information is selected, the controller 10 reads the three-dimensional image information associated with the selected patient M from the three-dimensional information storage 31 (step s3).

When the preparation for the surgical operation is performed in this manner, the controller 10 controls the three-dimensional position detector 60 to detect the three-dimensional positions of the operation worker and the patient M. This will be described in more detail. The controller 10 controls the microscope position detector 62 to detect the three-dimensional position of the dental three-dimensional microscope 50 (step s4), and controls the patient position detector 61 to detect the three-dimensional position of the patient M (step s5).

When the three-dimensional positions of the dental three-dimensional microscope 50 and the patient M are detected by the three-dimensional position detector 60, the controller 10 causes the relative position calculator 12 to detect the three-dimensional relative positions of the dental three-dimensional microscope 50 and the patient M (step s6). In this step, the image-capturing direction of the dental three-dimensional microscope 50 may be detected by the microscope position detector 62 performing position detection, or may be detected by the posture detector 53 included in the dental three-dimensional microscope 50. In this manner, the three-dimensional relative position of the dental three-dimensional microscope 50 with respect to the patient M and also the image-capturing direction of the dental three-dimensional microscope 50 with respect to the patient M are accurately detected.

The image-capturing direction detected by the microscope position detector 62 may encompass the direction along the direction of incidence of light entering the visible light three-dimensional camera 52, and also may encompass the image-capturing angular direction around the direction of incidence (direction of the line of sight) of the light entering the visible light three-dimensional camera 52, namely, the image-capturing direction (circumferential direction).

When the three-dimensional relative position of the dental three-dimensional microscope 50 with respect to the patient M is detected in this manner, the image generator 11 generates the three-dimensional captured image S based on the visible light image information captured by the visible light three-dimensional camera 52 (52*a* and 52*b*) of the dental three-dimensional microscope 50 and displays the three-dimensional captured image S in the main image display portion 110*a* (step s7).

When the surgical operation target selection operation button 159 is pressed, the controller 10 displays, by image recognition, dotted line BrL on the three-dimensional captured image S displayed on the main image display portion 110*a* such that a site that may be a surgical operation target site is selected (FIG. 3) (step s8). The controller 10 uses the cursor 163 to select the surgical operation target site on the three-dimensional display captured image S. When the surgical operation target site is selected on the three-dimensional captured image S (step s9), the image generator 11 generates the planar display-converted image Fp based on the three-dimensional image information read from the three-dimensional information storage 31, and displays the planar display-converted image Fp on the subordinate image display portion 110*b* (step s10).

Next, when the surgical operation content selection operation button 160 is pressed to select the surgical operation content to be performed on the selected surgical operation target site, a list of surgical operation contents that may be performed on the surgical operation target site is displayed in, for example, a pull-down manner such that one of the surgical operation contents may be selected (not shown) (step s11). One of the surgical operation contents is selected from the list (step s12). The surgical operation content is selected in order to, for example, automatically display a planar display-converted image Fp suitable to the surgical operation content in the subordinate image display portion 110*b* under the control of the controller 10. The surgical operation content does not need to be selected. Alternatively, it may be structured such that the surgical operation content cannot be selected.

In this embodiment, it is assumed that a root canal treatment is selected by which the roof of a molar tooth is cut away to expose the root canal orifice inside the tooth, and the tooth is cut to the root canal point by a file or reamer to treat the lesion in the root canal.

First, at the start of the treatment, as shown in FIG. 6A, the external shape, as seen in an articulation face direction, of the crown exposed from the gum of the molar tooth, which is the surgical operation target site, is displayed as the three-dimensional captured image S in the main image display portion 110*a*. For the selected root canal treatment, the position of the root canal orifice inside the molar tooth externally invisible, and the shape of the root canal, are very important. Therefore, the planar display-converted image Fp based on the x-ray three-dimensional image information acquired by the x-ray CT image-capturing device 40 is displayed in the subordinate image display portion 110*b*.

If, during the treatment, the orientation or the position of the dental three-dimensional microscope 50 is changed, namely, if the microscope position detector 62 or the posture detector 53 detects a movement of the dental three-dimensional microscope 50 (step s13: Yes) and the main and subordinate screen synchronization check box 158 on the display screen 100 is checked (step s14: Yes), the controller 10 causes the display direction adjuster 13 to adjust the magnification ratio in synchronization with the movement of the dental three-dimensional microscope 50. The adjustment is performed such that the display direction of the converted cross-sectional view Fp1 of the planar display-converted image Fp to be displayed in the subordinate image display portion 110*b* is parallel to the image captured by the microscope, namely, such that the collimation axes CL are parallel to each other, and such that the angles around the image-capturing axes are the same as each other. The controller 10 causes the display screen generator 14 to generate a converted cross-sectional view Fp1, the display direction of which has been adjusted by the display direction adjuster 13, and displays the converted cross-sectional view Fp1 in the subordinate image display portion 110*b* (step s19).

This will be described specifically. The dental three-dimensional microscope 50 is pivotable around an optical axis of the objective lens with respect to the support arm 58. As shown in FIG. 6B, when the orientation of the dental three-dimensional microscope 50 is rotated with respect to the surgical operation target site clockwise by a predetermined angle, the three-dimensional captured image S is displayed on the main image display portion 110*a* in accordance with the orientation. In synchronization with this, the converted cross-sectional view Fp1 is displayed in the subordinate image display portion 110*b* with an orientation changed clockwise by a predetermined angle. The axial direction of the optical axis of the objective lens matches the image-capturing direction (direction of the line of sight).

As shown in FIG. 6C, when the orientation of the dental three-dimensional microscope 50 is further rotated with respect to the surgical operation target site clockwise by a predetermined angle, the three-dimensional captured image S is displayed on the main image display portion 110a in accordance with the orientation. In synchronization with this, the planar display-converted image Fp is displayed in the subordinate image display portion 110b with an orientation changed clockwise by a predetermined angle. The orientation may be rotated counterclockwise.

The change in the image-capturing direction (circumferential direction) described above with reference to FIG. 6A through FIG. 6C is an example of pivoting of the dental three-dimensional microscope 50 around the optical axis of the objective lens. An angle around the optical axis of the objective lens is a specific example of angle around the image-capturing direction (direction of the line of sight). Such an angle may be visually recognized in, for example, a direction extending from the collimation axes CL on the three-dimensional captured image S and the converted cross-sectional views Fp1.

In this manner, mere movement of the position of the dental three-dimensional microscope 50 causes the orientation of the planar display-converted image Fp displayed in the subordinate image display portion 110b to be changed in synchronization therewith. Therefore, for example, the shape of the tooth root embedded in the gum, which cannot be not checked by observation in merely one direction, is checked.

Usually, it may be wished that the three-dimensional captured image S and the converted cross-sectional views Fp1 are observed in a synchronized state. Therefore, the check box 158 may be checked in a default state.

In the case where the movement of the dental three-dimensional microscope 50 is not detected (step s13: No), or in the case where the movement of the dental three-dimensional microscope 50 is detected but the main and subordinate screen synchronization check box 158 is not checked, the planar display-converted image Fp displayed in the subordinate image display portion 110b is not changed. When the subordinate screen display direction change operation button 156 is pressed in the state where the main and subordinate screen synchronization check box 158 is not checked and then an operation of adjusting the display direction of the planar display-converted image Fp displayed in the subordinate image display portion 110b is performed (step s16: Yes), the planar display-converted image Fp in the subordinate image display portion 110b is displayed with only the display direction being changed.

Now, an example of synchronizing a main screen and a subordinate screen will be described. Preferably, coordinate information is added to three-dimensional image information to be used to display the planar display-converted image Fp.

For example, it is assumed that the three-dimensional image information is acquired by the x-ray CT image-capturing device 40. The x-ray CT image-capturing device 40 usually includes a securing portion that secures a test subject at the time of x-ray CT image capturing. It is possible to calculate a spatial positional relationship between an x-ray generator and the securing portion. Therefore, it is also possible to calculate spatial coordinate information on an image-capturing target site of an image-capturing target such as the patient M secured to the securing portion.

For example, an XYZ rectangular coordinate system of a right-handed system is set, on the coordinate calculation, in a space where the x-ray CT image-capturing device 40 is installed. An up-down direction of the head of the image-capturing target is set as a "Z-axis direction". A direction crossing the Z-axis direction is set as an "X-axis direction". A direction crossing the Z-axis direction and the X-axis direction is set as a "Y-axis direction". The X-axis direction and the Y-axis direction may be arbitrarily defined. Herein, a left-right direction of the image-capturing target is set as the X-axis direction, and a front-rear direction of the image-capturing target is set as the Y-axis direction. A rightward direction as seen from the image-capturing target is set as the (+X) direction. A forward direction as seen from the image-capturing target is set as the (+Y) direction. A vertically upward direction is set as the (+Z) direction. Coordinate information on the image-capturing target, such as a three-dimensional position, an orientation or the like, is added to the three-dimensional image information.

An XYZ rectangular coordinate system of a right-hand system may also be set, on the coordinate calculation, in a space where the dental care table 22 is installed. For example, it is possible to calculate a spatial position of a surgical operation target holding portion such as the inclinable back seat 223, the head rest 224 or the like. Therefore, it is also possible to calculate spatial coordinate information on a surgical operation target site of the surgical operation target who is held by the surgical operation target holding portion. Especially, the head rest 224 holds the head of the surgical operation target, and is important to specify the position of the dental arch.

For example, an up-down direction of the head of the surgical operation target is set as a "Z-axis direction". A direction crossing the Z-axis direction is set as an "X-axis direction". A direction crossing the Z-axis direction and the X-axis direction is set as a "Y-axis direction". The X-axis direction and the Y-axis direction may be arbitrarily defined. Herein, a left-right direction of the surgical operation target in a sitting state is set as the X-axis direction, and a front-rear direction of the surgical operation target is set as the Y-axis direction. In this embodiment, a rightward direction as seen from the surgical operation target is set as the (+X) direction. A forward direction as seen from the surgical operation target is set as the (+Y) direction. A vertically upward direction is set as the (+Z) direction.

In the case where the image-capturing target and the surgical operation target are the same person, the XYZ rectangular coordinate of the x-ray CT image-capturing device 40 and the XYZ rectangular coordinate of the dental care table may be associated with each other by a coordinate calculation program, so that the position of the site captured by the x-ray CT image-capturing device 40 and observed by the dental three-dimensional microscope 50 may be matched with the position of the site, of the patient sitting on the dental care table 22, observed by the dental three-dimensional microscope 50. In this manner, the change in the display direction of the planar display-converted image Fp may be associated with the rotation of the dental three-dimensional microscope 50.

When, after only the display direction of the planar display-converted image Fp displayed in the subordinate image display portion 110b is changed, the main and subordinate screen synchronization check box 158 is checked (step s17), the display direction of the planar display-converted image Fp displayed in the subordinate image display portion 110b is returned to a direction matched to the display direction of the three-dimensional captured image S displayed in the main image display portion 110a, namely, to the direction before the change (step s18).

In the case where the image-capturing direction of the dental three-dimensional microscope 50 is changed while only the display direction of the planar display-converted image Fp displayed in the subordinate image display portion 110*b* is changed, even if the main and subordinate screen synchronization check box 158 is checked, the display direction of the planar display-converted image Fp displayed in the subordinate image display portion 110*b* is not returned to the display direction before the change, and the planar display-converted image Fp is displayed in a display direction in accordance with the post-change image-capturing direction of the dental three-dimensional microscope 50.

Now, a method for manually adjusting the display of the subordinate image display portion 110*b* displayed side by side with the main image display portion 110*a* during the surgical operation will be described.

When, for example, the subordinate screen size adjustment operation button 153 on the display screen 100 is pressed (step s20: Yes), as shown in FIG. 7A, a corner of the subordinate image display portion 110*b* is dragged with the cursor 163 to adjust the size of the subordinate image display portion 110*b* with respect to the three-dimensional captured image S to be displayed in the main image display portion 110*a* as shown in FIG. 7B (step s21).

In the case where, for example, the magnification ratio of the three-dimensional captured image S to be displayed in the main image display portion 110*a* is changed, the surgical operation target site of the three-dimensional captured image S to be displayed in the main image display portion 110*a*, and the subordinate image display portion 110*b* displaying the planar display-converted image Fp, may be possibly displayed in an overlapping manner. Therefore, the subordinate screen movement adjustment operation button 152 may be pressed (step s20) and the subordinate image display portion 110*b* may be dragged with the cursor 163, so that the size of the subordinate image display portion 110*b* with respect to the three-dimensional captured image S to be displayed in the main image display portion 110*a* is adjusted to be larger as shown in FIG. 7B or smaller as shown in FIG. 7C (step s21).

With reference to FIGS. 8A to 8F, such adjustment on the subordinate image display portion 110*b* with respect to the main image display portion 110*a* will be described in detail. As a specific example, adjustment on the size of the subordinate image display portion 110*b* will be described.

As shown in FIG. 8A, the three-dimensional captured image S is displayed three-dimensionally in the main image display portion 110*a* as follows. The left parallax image Sa (see FIG. 8B) captured by the left eye camera 52*a* and displayed in the left eye display portion 51*a* is collimated by the operation worker with his/her left eye via the left eye contact portion 57*a*. The right parallax image Sb (see FIG. 8C) captured by the right eye camera 52*b* and displayed in the right eye display portion 51*b* is collimated by the operation worker with his/her right eye via the right eye contact portion 57*b*. Thus, the operation worker visually recognizes the three-dimensional captured image S three-dimensionally.

This will be described in more detail. The left parallax image Sa captured by the left eye camera 52*a* and displayed in the left eye display portion 51*a* is conceptually displayed, for example, to the left of the three-dimensional image represented by the dashed line in FIG. 8B. The right parallax image Sb captured by the right eye camera 52*b* and displayed in the right eye display portion 51*b* is conceptually displayed, for example, to the right of the three-dimensional image represented by the dashed line in FIG. 8C. By contrast, the planar display-converted image Fp displayed in the subordinate image display portion 110*b* are at the same position and with the same size in the left eye display portion 51*a* and the right eye display portion 51*b*. As described above, the three-dimensional captured image S displayed three-dimensionally in the main image display portion 110*a*, and the planar display-converted image Fp displayed in the subordinate image display portion 110*b*, are different from each other in the relative positions of the surgical operation target site in the left parallax image Sa and the right parallax image Sb and the surgical operation target site displayed in the planar display-converted image Fp displayed two-dimensionally. The left parallax image Sa displayed in the left eye display portion 51*a* and the right parallax image Sb displayed in the right eye display portion 51*b* are different in the position or the size.

Now it is assumed that the operation worker visually and three-dimensionally recognizing the three-dimensional captured image S displayed in the main image display portion 110*a* shown in FIG. 8D performs an operation of dragging a corner of the subordinate image display portion 110*b* by a moving distance L to enlarge the subordinate image display portion 110*b*. In this case, as shown in FIG. 8F, in the right parallax image Sb, the pre-size adjustment distance between the corner of the subordinate image display portion 110*b* and the surgical operation target site is longer than the pre-size adjustment distance between the corner of the subordinate image display portion 110*b* in a visually and three-dimensionally recognized state and the surgical operation target site. In the right parallax image Sb, even if the subordinate image display portion 110*b* is enlarged in accordance with the moving distance L, the surgical operation target site in the main image display portion 110*a* and the subordinate image display portion 110*b* do not overlap each other.

By contrast, as shown in FIG. 8E, in the left parallax image Sa, the pre-size adjustment distance between the corner of the subordinate image display portion 110*b* and the surgical operation target site is shorter than the pre-size adjustment distance between the corner of the subordinate image display portion 110*b* in a visually and three-dimensionally recognized state and the surgical operation target site. In the left parallax image Sa, if the subordinate image display portion 110*b* is enlarged in accordance with the moving distance L, the surgical operation target site in the main image display portion 110*a* and the subordinate image display portion 110*b* overlap each other.

Thus, the controller 10 compares the left parallax image Sa and the right parallax image Sb regarding the pre-size adjustment distance between the corner of the subordinate image display portion 110*b* and the surgical operation target site, and converts the moving distance L of the drag operation for the three-dimensional captured image S visually and three-dimensionally recognized into an actual moving distance, based on the distance found to be shorter by the comparison. For example, the controller 10 performs control to adjust the size of the subordinate image display portion 110*b* with an assumption that the drag operation has been performed by a moving distance La shorter than the moving distance L as shown in FIG. 8E.

In the above, the size adjustment on the subordinate image display portion 110*b* is described. The controller 10 performs a similar adjustment for the position adjustment.

At least one of the size and the position of the subordinate image display portion 110*b* may be performed automatically by the controller 10 as long as the subordinate screen automatic adjustment operation button 151 is pressed.

FIGS. 6A to 6C and FIGS. 7A to 7C each show the external view of the surgical operation target site in the subordinate image display portion 110*b* as the planar display-converted image Fp. In the example of FIGS. 9A to 9D, a cross-sectional view of the surgical operation target site may be displayed in the subordinate image display portion 110*b* as the planar display-converted image Fp. When the subordinate screen display manner change operation button 155 is pressed, a list of various display manners including the external view, a horizontal cross-sectional view, a vertical cross-sectional view, a cross-sectional view in an optional direction, a frame view, a numerical value display and the like is displayed in a pull-down manner (not shown). When a desired display manner is selected (step s20: Yes), the planar display-converted image Fp in the selected display manner is displayed in the subordinate image display portion 110*b* (step s21).

Specifically, the subordinate screen display manner change operation button 155 is pressed and the horizontal cross-sectional view is selected from the list of the display manners displayed in the pull-down manner (not shown). When the horizontal cross-sectional view is selected, as shown in FIG. 9A, the horizontal cross-sectional view of the surgical operation target site is displayed in the subordinate image display portion 110*b* as the planar display-converted image Fp. In the case where the cross-sectional view in an optional direction is selected, a pop-up view (not shown) is provided such that the cross-sectional direction of the planar display-converted image Fp to be displayed in the subordinate image display portion 110*b* is designated. As shown in the figure, an image in the subordinate image display portion 110*b* based on which cross-sections may be designated may be used as a cross-sectional position designation display screen 180.

In the state where the horizontal cross-sectional view, the vertical cross-sectional view or the cross-sectional view in an optional direction is displayed in the subordinate image display portion 110*b*, the subordinate screen display site change operation button 154 may be pressed and one of the display position lines 181 may be selected in the cross-sectional position view Fp2 to designate the cross-sectional position. When the cross-sectional position is designated, as shown in each of FIG. 9B through FIG. 9D, the converted cross-sectional view Fp1 corresponding to the selected display position line 181 at a corresponding position in a depth direction perpendicular to the collimation axis CL in the tooth root is displayed in the subordinate image display portion 110*b*.

When a top display line 181*a* is selected as shown in FIG. 9B, the horizontal cross-sectional view corresponding to the top display line 181*a*, namely, the converted cross-sectional view Fp1*a*, is displayed in the subordinate image display portion 110*b* in the image display portion 110 shown in FIG. 9A. When a middle display line 181*b* is selected as shown in FIG. 9C, the converted cross-sectional view Fp1*b* is displayed in the subordinate image display portion 110*b* in the image display portion 110 shown in FIG. 9A. When a bottom display line 181*c* is selected as shown in FIG. 9D, the converted cross-sectional view Fp1*c* is displayed in the subordinate image display portion 110*b* in the image display portion 110 shown in FIG. 9A.

Even while any one of the cross-sectional views is displayed in the subordinate image display portion 110*b*, if the movement of the dental three-dimensional microscope 50 is detected, the planar display-converted image Fp, which is the cross-sectional view displayed in the subordinate image display portion 110*b*, may be changed in synchronization with the change in the display of the three-dimensional captured image S displayed in the main image display portion 110*a*, needless to say.

The cross-sectional position designation display screen 180 does not need to be displayed. The cross-sectional position of the planar display-converted image Fp displayed as the cross-sectional view in the subordinate image display portion 110*b* may be appropriately changed by the control of the controller 10 in accordance with the surgical operation content.

The display position lines 181 may set cross-sections in any of various manners. For example, a plurality of such cross-sections may have a large or small interval therebetween. A large number of cross-sections may be set, or a small number of cross-sections may be set (one cross-section may be set). Cross-sections (or a cross-section) may be set at any position.

Generally in the case of setting a plurality of cross-sections, a predetermined number of cross-sections may be prepared and located. Alternatively, the cross-sections may be made slidable, or an operation of designating the positions of the cross-sections may be acceptable, so that the cross-sections are set at any positions.

The above-described flow is repeated until the surgical operation is finished (step s22: No). The flow is completed when the surgical operation is finished (step s22: Yes).

Returning to FIG. 3, the collimation axes CL will be described. For the cross-sectional position view Fp2, no collimation axis CL needs to be used. As shown in a cross-sectional position view Fp3 in FIG. 14A, the collimation axis CL in each of the converted cross-sectional views Fp1 may be used as a line designating a cross-section. The collimation axis CL in each of the converted cross-sectional views Fp1 is, for example, an axis set in an X-Y plane.

In the cross-sectional position view Fp3, a target tooth is displayed such that the tooth axis is parallel in an up-down direction of the screen. A plane in which the collimation axis CL extends in a Z-axis direction is the designated cross-section. A figure of the designated cross-section is displayed. The display position lines 181 may be displayed. An operation of setting, on the converted cross-sectional views Fp1, a line designating a cross-section without using any collimation axis CL may be acceptable.

Figure 14A:
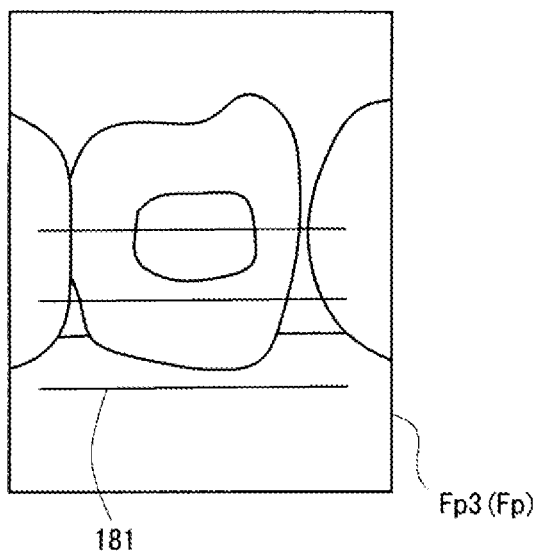
FIGS. 14A and 14B show a cross-sectional position in a display screen in another embodiment.
Figure 14B:
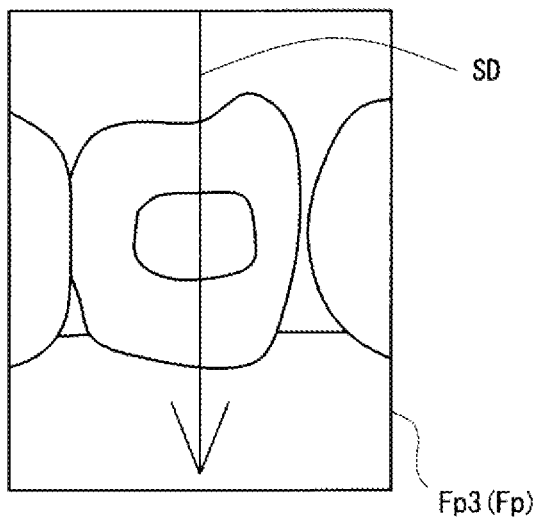

In FIG. 14A, the cross-sectional position view Fp3 is displayed instead of the cross-sectional position view Fp2. Both of the cross-sectional position view Fp2 and the cross-sectional position view Fp3 may be displayed side by side. The cross-sectional position view Fp2 and the cross-sectional position view Fp3 may be displayed in a switched manner. As shown in a cross-sectional position view Fp4 in FIG. 14B, an index SD indicating the image-capturing direction (direction of the line of sight) may be displayed.

An example of setting the collimation axis CL will be described. The collimation axis CL may be set in a direction that is along the dental arch and crosses each tooth at the center of a direction between the buccal side and the lingual side, as seen in a plan view. For the entirety of the dental arch, the collimation axis may be set in a generally horseshoe-shape crossing each tooth at the center of the direction between the buccal side and the lingual side.

The collimation axis CL may be set in another direction. For example, any direction may be acceptable as the direction of the collimation axis CL for each of the converted cross-sectional views Fp1. Alternatively, a default direction, for example, an X direction, a Y direction, or a direction synthesizing the X direction and the Y direction, may be set on an X-Y plane.

The collimation axis CL may be displayed on the three-dimensional captured image S and also on each of the converted cross-sectional views Fp1, so that the direction is easily assumed even if the three-dimensional captured image S and the converted cross-sectional views Fp1 are not synchronized with each other.

As described above, the collimation axis CL is used as a visual recognition index indicating a direction common to the three-dimensional captured image S and the converted cross-sectional views Fp1. Preferably, the collimation axis CL is set at a common position in the three-dimensional captured image S and the converted cross-sectional views Fp1.

The dental care system 1, including the observation system 3, includes the visible light three-dimensional camera (52a and 52b) capturing the three-dimensional captured image S of a desired surgical operation target site in the oral cavity region; the relative position calculator 12 detecting the image-capturing direction of the visible light three-dimensional camera 52 (52a and 52b) with respect to the surgical operation target site; the three-dimensional information storage 31 storing the three-dimensional image information on the oral cavity region acquired in advance; the image display portion 110 displaying, side by side, the three-dimensional captured image S captured by the visible light three-dimensional camera 52 (52a and 52b) and the planar display-converted image Fp based on the three-dimensional image information corresponding to the surgical operation target; and the display direction adjuster 13 displaying, in the image display portion 110, the planar display-converted image Fp in a predetermined direction on the basis of the image-capturing direction detected by the relative position calculator 12. Therefore, according to the dental care system 1 and the method for displaying the three-dimensional captured image S using the observation system 3, the three-dimensional captured image S of the desired surgical operation target site in the oral cavity region captured by the visible light three-dimensional camera 52 (52a and 52b), and the three-dimensional image information on the desired surgical operation target site in the oral cavity region acquired in advance, do not overlap each other, and the invisible portion in the three-dimensional captured image S is easily recognized.

This will be described in detail. The image-capturing direction of the visible light three-dimensional camera 52 (52a and 52b), performing three-dimensional capturing of the three-dimensional captured image S of a desired surgical operation target site in the oral cavity region, with respect to the surgical operation target site is detected. The three-dimensional captured image S captured by the visible light three-dimensional camera 52 (52a and 52b), and the planar display-converted image Fp based on the three-dimensional image information that corresponds to the surgical operation target site and is acquired in advance and stored on the three-dimensional information storage 31, are displayed side by side in the image display portion 110. The planar display-converted image Fp in a predetermined direction on the basis of the image-capturing direction detected by the relative position calculator 12 is also displayed.

Therefore, for example, in the state where the planar display-converted image Fp based on the three-dimensional image information does not overlap the three-dimensional captured image S of the surgical operation target site, the planar display-converted image Fp in the image-capturing direction of the three-dimensional captured image S of the surgical operation target site is displayed side by side with the three-dimensional display captured image S. In addition, the planar display-converted image Fp is displayed in a direction facing the three-dimensional display captured image S. Therefore, the operation worker may perform the surgical operation safely and accurately while checking the planar display-converted image Fp displaying the invisible portion of the corresponding image side by side with the invisible portion of the visible image and also checking the three-dimensional captured image S clearly displaying the surgical operation target site.

The subordinate screen display direction change operation button 156 usable to operate the change in the display direction of the planar display-converted image Fp, and the main and subordinate screen synchronization check box 158 usable to perform an operation of returning the planar display-converted image Fp, the display direction of which has been changed, to the direction corresponding to the image-capturing direction are provided. Therefore, the operation worker may adjust only the display direction of the planar display-converted image Fp by use of the subordinate screen display direction change operation button 156 in accordance with the surgical operation. Even after the display direction of the planar display-converted image Fp is changed, the main and subordinate screen synchronization check box 158 may be operated to display the planar display-converted image Fp, the display direction of which has been changed, in accordance with the image-capturing direction of the three-dimensional captured image S with no need to fine-tune the display direction of the planar display-converted image Fp.

Even in the case where the display direction of the planar display-converted image Fp is adjusted by use of the subordinate screen display direction change operation button 156 and after that, the image-capturing direction of the dental three-dimensional microscope 50 is adjusted, the post-adjustment display direction of the planar display-converted image Fp is matched to the post-adjustment image-capturing direction of the dental three-dimensional microscope 50. Therefore, the convenience and the operability are improved as compared with the case where the post-adjustment display direction of the planar display-converted image Fp is manually fine-tuned to the post-adjustment image-capturing direction of the dental three-dimensional microscope 50.

The three-dimensional image information includes any one of the three-dimensional x-ray image acquired by the x-ray CT image-capturing device, the nuclear magnetic resonance image acquired by the nuclear magnetic resonance image-capturing device, the ultrasonic three-dimensional image acquired by the ultrasonic diagnostic image-capturing device, and the optical interference three-dimensional image acquired by the optical interference tomographic image-capturing device. Therefore, for example, the three-dimensional image of a type suitable to the surgical operation content or the patient is usable as the three-dimensional image information.

The horizontal cross-sectional view perpendicular to the image-capturing direction (direction of the line of sight) based on the three-dimensional image information, the vertical cross-sectional view in the image-capturing direction (direction of the line of sight), or the cross-sectional view of an optional direction with respect to the image-capturing direction (direction of the line of sight) are displayed in the subordinate image display portion 110b as the planar display-converted image Fp. Therefore, the invisible portion in the surgical operation target site is recognized more easily and more accurately by the cross-sectional view. Thus, the surgical operation is performed more safely and more accurately.

The display direction adjuster 13 includes the cross-sectional position designation display screen 180 usable to adjust the cross-sectional position of the cross-sectional view based on the image-capturing direction (direction of the line of sight). Therefore, the cross-sectional view of the invisible portion at a desired cross-sectional position in the image-capturing target is displayed in the image display portion 110. The portion of interest in the invisible portion is recognized more easily and more accurately. Thus, the surgical operation is performed more safely and more accurately.

The image display portion 110 includes the subordinate image display portion 110b displaying the planar display-converted image Fp, and also includes the subordinate screen movement adjustment operation button 152 and the subordinate screen size adjustment operation button 153 adjusting at least one of the size and the position of the subordinate image display portion 110b in the image display portion 110. Therefore, for example, the subordinate image display portion 110b displaying the planar display-converted image Fp may be position-adjusted to a position that is more easily recognized, enlarged or diminished in accordance with, for example, the size of the image-capturing target site or the surgical operation content. Thus, the main portion of the three-dimensional captured image S displayed in the main image display portion 110a and the subordinate image display portion 110b displaying the planar display-converted image Fp do not overlap each other. A demand of the operation worker is precisely fulfilled, and the degree of satisfaction of the operation worker is improved.

The relative positions of the surgical operation target site in each of the left parallax image Sa and the right parallax image Sb, and the subordinate image display portion 110b, are different from each other. In the case where the subordinate screen movement adjustment operation button 152 and the subordinate screen size adjustment operation button 153 are used to adjust the subordinate image display portion 110b, there may be an undesirable possibility that even if the surgical operation target site in one of the left parallax image Sa and the right parallax image Sb does not overlap the subordinate image display portion 110b, the surgical operation target site in the other of the left parallax image Sa and the right parallax image Sb overlaps the subordinate image display portion 110b. However, the adjustment on the subordinate image display portion 110b by use of the subordinate screen movement adjustment operation button 152 and the subordinate screen size adjustment operation button 153 is performed such that the surgical operation target site in each of the left parallax image Sa and the right parallax image Sb does not overlap the subordinate image display portion 110b based on the positional relationship between the selected surgical operation target site in each of the left parallax image Sa and the right parallax image Sb corresponding to the three-dimensional captured image S and the subordinate image display portion 110b. Therefore, the surgical operation target site displayed three-dimensionally and the subordinate image display portion 110b displayed two-dimensionally are displayed side by side with no overlapping.

The subordinate screen display manner change operation button 155 usable to switch the display manner of the planar display-converted image Fp is provided. Therefore, for example, data suitable to the surgical operation such as a cross-sectional view, volume data, numerical data or the like is displayed as the planar display-converted image Fp.

Instead of the planar display-converted image Fp, dental care data may be displayed in the image display portion 110. In this case, for example, more precise surgical operation is performed while the dental care data such as the surgical operation content in the past or the like is checked. The image display portion 110 may display the dental care data together with the planar display-converted image Fp.

The image display portion 110 may be displayed in the display portion 51 (51a and 51b) of the HMD 510 or the HUD 520 attachable to the operation worker. The visible light three-dimensional camera 52 (52a and 52b) may include a pair of cameras 52a and 52b. In the case where the image display portion 110 includes the cameras 52a and 52b, the visible light three-dimensional camera 52 is supported by the support arm 58 extending from the head rest 224 of the chair unit 2 such that the position of the three-dimensional camera 52 is freely changeable. Therefore, the operation worker may perform the surgical operation by use of a device having more suitable specifications more in accordance with the surgical operation content or preference.

The visible light three-dimensional camera 52 (52a and 52b) includes the blur prevention mechanism 54 preventing a blur. Therefore, the surgical operation is performed while a clearer three-dimensional captured image S is checked.

The visible light three-dimensional camera 52 (52a and 52b) includes the mirror image reversal mechanism 55 performing mirror image reversal of the three-dimensional captured image S. Therefore, the operation worker may perform the surgical operation while checking the mirror-reversed three-dimensional captured image S. Such a manner of performing the surgical operation is similar to the manner of performing the surgical operation while checking a dental mirror, to which the operation worker is accustomed.

In the case where the dental mirror is used, the controller 10 may include a mirror image reversal portion (not shown) performing mirror image reversal of the three-dimensional image such as the x-ray CT image or the like. In this manner, the three-dimensional image may be displayed in a manner of mirror image reversal. When necessary, the three-dimensional image may be rotated to a direction in which the three-dimensional image is easily recognized by the operation worker and displayed.

FIGS. 12A to 12E shows an example in which the observation is made in different directions. As shown in FIG. 12A, a tooth TH is observed by the dental three-dimensional microscope 50 located at a position PS1 along an optical axis SV1 of the objective lens. In the state shown in this figure, the axial direction of the optical axis SV1 and the axial direction of the tooth axis of the tooth TH generally match each other.

From this state, the dental three-dimensional microscope 50 is moved to a position PS2, and the tooth TH is observed along an optical axis SV2 of the objective lens. The optical axis SV2 is at an angle $\theta\alpha$ with respect to the optical axis SV1. A cross-section of the tooth TH along a display position line 181 is set. The cross-section is perpendicular to the optical axis SV1. A converted cross-sectional view Fp1 taken along the display position line 181 is displayed as shown in FIG. 12C.

In the case where the tooth TH is observed along the optical axis SV2, as shown in FIG. 12B, a cross-section taken along a display position line 181 perpendicular to the optical axis SV2 is set. The cross-sectional position may be kept the same as that of the cross-section perpendicular to the optical axis SV1.

In this case, when the cross-section is viewed in a direction of line of sight along the optical axis SV2, visual compression occurs in a direction in which the dental three-dimensional microscope 50 is inclined. A converted cross-sectional view in accordance with this is displayed as shown in FIG. 12D.

The change in the converted cross-section Fp1 caused by the change in the image-capturing direction (circumferential direction) may be performed at the same circumferential direction display angle even though there is visual compression. Regardless of the inclination of the dental three-dimensional microscope 50, the converted cross-section Fp1 as shown in FIG. 12C may be displayed.

The cross-section taken along the display position line 181 may be parallel to the X-Y plane or a plane perpendicular to the axial direction of the tooth axis of the tooth TH. Alternatively, any other default plane may be set as the cross-section taken along the display position line 181.

The cross-section shown in the converted cross-sectional view Fp1 may be set as follows. Because of the structure of the teeth and the relationship between the teeth and the axis of the head, the teeth in the lower jaw are often looked down or obliquely looked down in a downward image-capturing direction (direction of the line of sight), and the teeth in the upper jaw are often looked up or obliquely looked up in an upward image-capturing direction (direction of the line of sight). Therefore, it is preferred that the cross-section is set to cross the tooth axis. With such a setting, the state of the cross-section at a position deeper than the tooth surface that is reflected in the three-dimensional captured image S actually observed by the operation worker is grasped. For this purpose, it may be conceived to set a cross-section perpendicular to the direction of line of sight as described above, or a cross-section perpendicular to the axial direction of the tooth axis of the tooth.

It is preferred that the cross-section is observed in a direction from the crown to the tooth root or in an opposite direction thereto in order to grasp well the state inside the target tooth. In the case where a plurality of converted cross-sectional views Fp1 are provided, it is preferred that the cross-sectional views Fp1 are positionally arranged in a direction connecting the crown and the tooth root. For example, in the case where the image-capturing direction is the direction of line of sight along the optical axis SV2 as shown in FIG. 12B, a cross-section taken along the display position line 181 perpendicular to the optical axis SV2 may be set. In the case where a plurality of such cross-sections are set, it is preferred that as shown in FIG. 12E, the plurality of cross-sections (the plurality of converted cross-sectional views Fp1) are positionally arranged along a tooth axis TX of the target tooth.

The setting of the cross-section will be described in more detail. It is assumed that the cross-section taken along the display position line 181 has a maximum angle AMX and a minimum angle AMN with respect to the tooth axis TX. Preferably, the angle AMX is 90 degrees or larger and 130 degrees or smaller. The angle AMN is 45 degrees or larger and 90 degrees or smaller. A state where the angle AMX and the angle AMN are 90 degrees is of the extremum. As the angle AMX and the angle AMN are closer to 90 degrees, a cross-section as obtained by slicing the target tooth, namely, a cross-section easier to grasp, is provided. Where the angle of the optical axis SV2 with respect to the tooth axis TX is angle AOB, the angle AOB may be set to fulfill 90°–angle AMN<angle AOB (when angle AOB=0°, angle AMN=90°).

The axial direction of the tooth axis TX may be found based on the spatial coordinate information on the surgical operation target holding portion of the dental care table 22 and the spatial coordinate information on (the dental arch of) the surgical operation target held by the surgical operation target holding portion. A surgical operation target having a standard skeleton generally assumed may be set, or data on an axial direction of the tooth axis may be obtained from measurement information on an individual surgical operation target.

With reference to FIGS. 13A to 13C, the image-capturing direction (direction of the line of sight), specifically, an axial direction of an optical axis of the objective lens, and the direction of the planar display-converted image Fp will be described. As shown in FIG. 13A, a tooth THU in the upper jaw and a tooth THL in the lower jaw are assumed. A point BU on the buccal side and a point PU on the lingual side are set in a surface layer of the tooth THU in the upper jaw. A point BL on the buccal side and a point PL on the lingual side are set in a surface layer of the tooth THL in the lower jaw.

The tooth THU in the upper jaw is observed by the dental three-dimensional microscope 50 along an optical axis SV3 of the objective lens, and the tooth THL in the lower jaw is observed by the dental three-dimensional microscope 50 along an optical axis SV4 of the objective lens. The tooth THU in the upper jaw and the tooth THL in the lower jaw are each displayed in the three-dimensional captured image S and the planar display-converted image Fp.

FIG. 13B shows the tooth THU in the upper jaw. In the case where the three-dimensional captured image S displays the point BU in an upper part thereof and displays the point PU in a lower part thereof, the planar display-converted image Fp also displays the point BU in an upper part thereof and displays the point PU in a lower part thereof.

FIG. 13C shows the tooth THL in the lower jaw. In the case where the three-dimensional captured image S displays the point PL in the upper part thereof and displays the point BL in the lower part thereof, the planar display-converted image Fp also displays the point PL in the upper part thereof and displays the point BL in the lower part thereof. In this manner, the direction of the cross-section to be displayed in the planar display-converted image Fp is set based on the image-capturing direction (direction of line of light). (In accordance with whether the tooth is looked down or looked up, the cross-section is displayed as being looked up or looked down.)

The visible light image according to the present invention corresponds to the three-dimensional captured image S in the above-described embodiment; and similarly, the three-dimensional camera corresponds to the visible light three-dimensional camera 52;

the image-capturing site corresponds to the surgical operation target site;

the image-capturing direction detector corresponds to the relative position calculator 12;

the storage corresponds to the three-dimensional information storage 31;

the corresponding image corresponds to the planar display-converted image Fp;

the display portion (the display) corresponds to the image display portion 110;

the image processor corresponds to the display direction adjuster 13;

the dental observation device corresponds to the observation system 3;

the display direction change operator corresponds to the subordinate screen display direction change operation button 156;

the display direction reset operator corresponds to the main and subordinate screen synchronization check box 158;

the cross-section adjustment operator corresponds to the cross-sectional position designation display screen 180;

the corresponding image display region corresponds to the subordinate image display portion 110b;

the region adjuster corresponds to the subordinate screen movement adjustment operation button 152 and the subordinate screen size adjustment operation button 153;

the display switch operator corresponds to the subordinate screen display manner change operation button 155;

the head-mountable display portion corresponds to the HMD 510 and the HUD 520;

the support arm corresponds to the support arm 58;

the blur prevention mechanism corresponds to the blur prevention mechanism 54; and the mirror image reversal mechanism corresponds to the mirror image reversal mechanism 55.

The present invention is not limited to the above-described embodiment.

For example, in the root canal treatment of cutting the tooth described above as the surgical operation content, the planar display-converted image Fp based on the x-ray three-dimensional image information is displayed in the subordinate image display portion 110b. Alternatively, for example, a surgical operation for a tooth T with caries may be performed while a shape usable to form an abutment tooth X as shown in FIG. 11B is displayed in the subordinate image display portion 110b.

In the case where the abutment tooth X is displayed in the subordinate image display portion 110b, the invisible portion in the image-capturing target site is of a shape formed by the surgical operation, and the shape is displayed as the three-dimensional image information side by side with the visible light image. Thus, the dental observation system may act as a surgical operation assistant or a surgical operation simulator.

The visible light three-dimensional camera 52 (52a and 52b) in the above-described embodiment may capture, three-dimensionally, the image of the surgical operation target site, which is the observation target, and is a two-lens microscope that performs the observation using the parallax between the left and right eyes. Alternatively, a device, such as an RGB-D camera or a light field camera, including both of a component detecting RGB signals as the three primary colors of light and a component detecting the distance, or a device capturing a plurality of different blurred images with one lens at high speed and processes the blurred images to provide a three-dimensional image, may be used as a head mountable display with a camera or a device that includes a single lens but acquires depth information.

The following structure may be used regarding the adjustment on the position of the subordinate image display portion 110b in the image display portion 110. When the planar display-converted image Fp in the subordinate image display portion 110b is displayed as overlapping the three-dimensional captured image S in the main image display portion 110a, the planar display-converted image Fp gradually becomes transparent, namely, the degree of transparency of the planar display-converted image Fp is adjusted in accordance with the degree of overlapping of the three-dimensional captured image S and the planar display-converted image Fp.

In the above, the main and subordinate screen synchronization check box 158 acts as the display direction reset operator. A display return operator button or the like acting as the display direction reset operator may be provided separately from the main and subordinate screen synchronization check box 158.

REFERENCE SIGNS LIST

3 . . . observation system
12 . . . relative position calculator
13 . . . display direction adjuster
31 . . . three-dimensional information storage
52 . . . visible light three-dimensional camera
54 . . . blur prevention mechanism
55 . . . mirror image reversal mechanism
58 . . . support arm
110 . . . image display portion
110b . . . subordinate image display portion
152 . . . subordinate screen movement adjustment operation button
153 . . . subordinate screen size adjustment operation button
155 . . . subordinate screen display manner change operation button
156 . . . subordinate screen display direction change operation button
158 . . . main and subordinate screen synchronization check box
180 . . . cross-sectional position designation display screen
510 . . . HMD
520 . . . HUD
Fp . . . planar display-converted image
S . . . three-dimensional captured image

What is claimed is:

1. A dental observation device, comprising:
a camera performing image capturing of a left parallax image and a right parallax image of a desired image-capturing site in an oral cavity region;
a direction detector detecting an image-capturing direction of the camera for the image-capturing site;
a storage storing three-dimensional image information on the oral cavity region acquired by CT imaging in advance;
a processor generating a three dimensional captured image by processing the left and right parallax image captured by the camera, and the processor also generating a planar display converted image corresponding to the desired image-capturing site by converting the stored three-dimensional image information into two-dimensional sectional image; and
a display displaying, side by side, the three dimensional captured image and the planar display converted image;
wherein the three-dimensional captured image of the image-capturing site is displayed three-dimensionally,
the planar display converted image is displayed two-dimensionally,
both being viewed in a direction parallel to the image-capturing direction,
a cross section of the planar display converted image is set perpendicular to the image-capturing direction, and the planar display converted image being viewed at the same angle around the image-capturing direction as that of the three-dimensional captured image; and wherein when the image-capturing direction is changed, the cross section of the planar display converted image remains perpendicular to the image-capturing direction.

2. The dental observation device according to claim 1, wherein:
the display includes a corresponding image display region in which the planar display converted image is allowed to be displayed, and also includes a region adjuster adjusting at least one of a size and a position of the corresponding image display region in the display.

3. The dental observation device according to claim 2, further comprising a surgical operation target selector selecting a surgical operation target site in the three-dimensional captured image of the image-capturing site;
wherein based on the positional relationship between the surgical operation target site, selected by the surgical operation target selector, and the corresponding image display region, the region adjuster adjusts the corresponding image display region such that the surgical operation target site and the corresponding image display region do not overlap each other.

4. The dental observation device according to claim 1, further comprising:
a display direction change operator operating a change in the display direction of the planar display converted image from a direction corresponding to the image-capturing direction; and
a display direction reset operator performing an operation of returning the display direction of the planar display converted image, which has been changed, to the direction corresponding to the image-capturing direction.

5. The dental observation device according to claim 1, wherein the three-dimensional image information represents a three-dimensional x-ray image acquired by an x-ray CT image-capturing device.

6. The dental observation device according to claim 5, wherein based on the three-dimensional image information, the processor causes the display to display a cross-sectional image in a direction based on the image-capturing direction, the cross-sectional image being displayed as the planar display converted image.

7. The dental observation device according to claim 6, wherein the processor includes a cross-section adjustment operator adjusting a cross-sectional position in a direction based on the image-capturing direction of the cross-sectional image.

8. The dental observation device according to claim 1, further comprising a display switch operator switching the manner of display of the planar display converted image.

9. The dental observation device according to claim 1, wherein the display displays at least one of dental care data among a measured root canal length value, a shaving torque value and a shaving rotation rate instead of, or in addition to, the planar display converted image.

10. The dental observation device according to claim 1, wherein the display is a head-mountable display mountable on a head of an operation worker.

11. The dental observation device according to claim 1, wherein the camera is a dental microscope held by a support arm extending from a side of a dental care device such that the position of the camera is changeable.

12. The dental observation device according to claim 1, wherein the camera includes a blur prevention mechanism preventing a blur.

13. The dental observation device according to claim 1, wherein the camera includes a mirror image reversal mechanism performing mirror image reversal on the three-dimensional captured image.

14. A method for displaying a dental image, comprising the steps of:
performing, by a camera, image-capturing of a left parallax image and a right parallax image of a desired image-capturing site in an oral cavity region; and
detecting an image-capturing direction of the camera for the image-capturing site; processing to generate a three dimensional captured image by processing the left and right parallax image captured by the camera, and also processing to generate a planar display converted image by converting a three-dimensional image information on the oral cavity region acquired by CT imaging in advance into two-dimensional sectional image;
displaying, side by side, the three dimensional captured image and the planar display converted image;
wherein the three-dimensional captured image of the image-capturing site is displayed three-dimensionally, the planar display converted image is displayed two-dimensionally, both being viewed in a direction parallel to the image-capturing direction, a cross section of the planar display converted image is set perpendicular to the image-capturing direction, and the planar display converted image being viewed at the same angle around the image-capturing direction as that of the three-dimensional captured image; and
wherein when the image-capturing direction is changed, the cross section of the planar display converted image remains perpendicular to the image-capturing direction.

15. A dental observation device, comprising:
a camera;
a storage;
a direction detector;
a display; and
a processor;
wherein:
the camera performs image capturing of a left parallax image and a right parallax image of a desired image-capturing site in an oral cavity region;
the storage stores three-dimensional image information on the oral cavity region acquired by CT imaging in advance;
the direction detector detects an image-capturing direction of the camera for the image-capturing site; and
the processor generating a three dimensional captured image by processing the left and right parallax image captured by the camera, and the processor also generating a planar display converted image by converting the stored three-dimensional image information into two-dimensional sectional image;
wherein the three-dimensional captured image of the image-capturing site is displayed three-dimensionally, the planar display converted image is displayed two-dimensionally, both being viewed in a direction parallel to the image-capturing direction, a cross section of the planar display converted image is set perpendicular to the image-capturing direction, and the planar display converted image being viewed at the same angle around the image-capturing direction as that of the three-dimensional captured image; and wherein when the image-capturing direction is changed, the cross section of the planar display converted image remains perpendicular to the image-capturing direction.

16. The dental observation device according to claim 15, wherein the three-dimensional image information represents a three-dimensional x-ray image acquired by an x-ray CT image-capturing device.

17. The dental observation device according to claim 16, wherein based on the three-dimensional image information, the processor causes the display to display a cross-sectional image in a direction based on the image-capturing direction, the cross-sectional image being displayed as the planar display converted image.

18. The dental observation device according to claim 17, wherein the processor accepts a cross-section adjustment operation of adjusting a cross-sectional position in a direction based on the image-capturing direction of the cross-sectional image.

* * * * *